United States Patent [19]
Gebert et al.

[11] Patent Number: 5,965,555
[45] Date of Patent: Oct. 12, 1999

[54] XANTHINE COMPOUNDS HAVING TERMINALLY ANIMATED ALKYNOL SIDE CHAINS

[75] Inventors: Ulrich Gebert, Glashütten; Elisabeth Defossa, Idstein; Uwe Heinelt, Wiesbaden; Karl Rudolphi, Mainz; John J. Grome, Wiesbaden, all of Germany

[73] Assignee: Hoechst Aktiengesellschaft, Frankfurt am Main, Germany

[21] Appl. No.: 08/866,347

[22] Filed: May 30, 1997

[30] Foreign Application Priority Data

Jun. 7, 1996 [DE] Germany .............................. 196 22 734
Sep. 11, 1996 [DE] Germany .............................. 196 36 882

[51] Int. Cl.⁶ ..................... C07D 473/04; C07D 473/06; A61K 31/52; C07F 7/10
[52] U.S. Cl. .................................. 514/228.5; 514/234.2; 514/263; 544/61; 544/118; 544/229; 544/272
[58] Field of Search .................................. 544/229, 272, 544/61, 118; 514/228.5, 234.2, 263

[56] References Cited

U.S. PATENT DOCUMENTS 4,007,197  2/1977  Christensen et al. ................... 260/293

FOREIGN PATENT DOCUMENTS

| 0 223 403 A2 | 5/1987 | European Pat. Off. . |
| 0 260 127 A2 | 3/1988 | European Pat. Off. . |
| 0 369 744 A2 | 5/1990 | European Pat. Off. . |
| WO 87/00523 | 1/1987 | WIPO . |
| WO 94/11001 | 5/1994 | WIPO . |
| WO 95/15155 | 6/1995 | WIPO . |

OTHER PUBLICATIONS

Chalmers, TiPS 17, 166 Apr. 1996.
Cai, Helv. Chim. Acta 78, 732, 1995.
Ohnuma, Te. Letters 27, 219, 1986.
Mulzer, Ann. Chem 1992, 1131, 1992.
Abel, Angnew. CHem 106, 2522, 1994.
Peruche, Pharmazeutische Zeitung 1994, 139/31, 2482–3.
Lyrer, Schweiz. Med. Wochenschr. 1994, 124/45, 2005–12.
Sandercock et al, Lancet 1992, 339/8792, 537–9.
Leys et al, Rev. Med. Interne 1994,, 15/5, 350–6. (Abstract only).
Fisher, Stroke 1990, 21/8 Suppl. 1, I–130–I–131.
Puruche et al, Prog. Neuropsychopharmacol. Biol. Psychiatry 1993, 17/1, 20–70.
Ferrer et al, Clin. Neuropharmacol. 1990, 13 Suppl. 3, S9–S25.
Sila et al, Drugs 1988, 35/4, 468–76.
Frampton et al, Drugs & Aging 1995, 7/6, 480–503.
Uldry et al, Schweiz., Rundsch. Med. Prax. 1989, 78/23, 663–6.
Parkinson et al, Gen. Pharmac. 1994, 25/6; 1053–8.
Williams, Drug Dev. Res. 1993, 28/3, 438–44.
Huber et al, J. Cereb. Blood Flow Metab. 1993, 13/3, 526–30. (Abstract only).
Corriu et al, Tetrahedron 1992, 48/30, 6231–44.
Lundkvist et al, J. Med. Chem. 1990, 33, 3182–9.
Imamoto et al, Tetrahedron Letters 1984, 25/38, 4233–6.
Lyrer, Schweiz. Med. Wochenschr. 1994, 124,45, 2005–12.
Rudolphi et al, J. Cereb. Blood Flow Metab. 1987, 7/1, 74–81.
Tamura et al, J. Cereb. Blood Flow Metab. 1981, 1, 53–60.
Bederson et al, Stroke 1986, 17, 472–76.
Park et al, Neurosci. Lett. 1992, 147, 41–44.
Park et al, Neurosci. Lett. 1994, 178, 235–238.
Backhauss et al, J. Pharm. Meth. 1992, 27, 27–32.
Zue et al, Brain Res. 1992, 587, 66–72.
Weygang/Hilgetag: Organisch Chemische Experimentierkunst 4. Auf. (1970) 990–993.
Pschyrembel Klinisches Wöterbuch 255. Auf. Walter de Gruter (1986) 105 +1840.
RÖMPP Chemie Lexikon 9. Auf., Band 4 (1991) 2632 +2954.
Chemical Abstract 70:37787h (1969), Johannes Reisch, "Synthesis and effect of drugs. VI. Preparation of some N–alkynyl xanthine derivatives". (Inst. Pharm. Chem. Westf. Wilheims–Univ., Muenster/Westf., *Arzneim–Forsch*, 1968, 18(11), 1485–6.
Chemical Abstract 88:68922Z (1978), Johannes Reisch, et al., "The Synthesis and activity of potential drugs, part 14, Metabolism 7–(3–butynyl)theophylline in rats.", (Inst. Pharm. Chem., Westfael. Wilhelms–Univ., Muenster, *Arch Pharm.* (Weinheim) 1977, 310(11), 888–93.

*Primary Examiner*—Mark L. Berch
*Attorney, Agent, or Firm*—Finnegan, Henderson, Farabow, Garrett & Dunner, L.L.P.

[57] ABSTRACT

Compounds of the formula I,

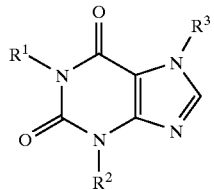

in which one of the radicals $R^1$ and $R^3$ is an alkynol residue of the formula Ia or Ib

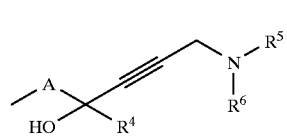

(Ia)

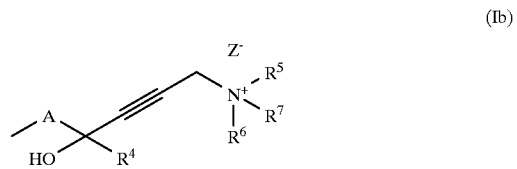

(Ib)

are suitable for producing pharmaceuticals having a neuroprotective effect.

15 Claims, No Drawings

XANTHINE COMPOUNDS HAVING TERMINALLY ANIMATED ALKYNOL SIDE CHAINS

BACKGROUND OF THE INVENTION

The invention relates to novel xanthine derivatives having at least one alkynol side chain in position 1 or 7 of the xanthine framework, processes for their preparation and their use as active substances in pharmaceuticals, in particular for the treatment and/or prophylaxis of cerebrovascular disorders characterized by damage caused by ischemia and subsequent necrotic destruction of nerve cells (neurons).

Postischemic neuronal cell death and the fatal functional deficits caused thereby, with correspondingly serious neurological and/or psychological symptoms, are the common clinical picture of a large number of cerebrovascular disorders. These include, for example, stroke; transient ischemic attacks (TIA); multiinfarct dementia, dementia of the mixed type with vascular and degenerative (Alzheimer) components; spinal cord damage; brain trauma as a result of head injuries; and neuronal damage after cardiac arrest, (neonatal) asphyxia and resuscitation, and vascular surgical operations (for example bypass operations) in the region of the main arteries supplying the brain.

In clinical practice it is stroke which predominates, also called cerebrovascular accident, apoplexy, cerebral apoplexia or apoplectic insult. It is the basic cause of about 15% of all deaths (Pschyrembel, Klinisches Wörterbuch [Clinical Dictionary] Walter de Gruyter-Verlag, 255th edition, 1986, page 105) and is thus in third place after heart disease and cancers in the statistics of the causes of deaths (Pharmazeutische Zeitung 1994, 139/31: 2482–2483). Women and men are equally affected, there being a drastic increase in morbidity after the 6th decade. The incidence is currently about 0.8% of the world population with a continuous increase in prevalence, especially in industrialized countries because the average life expectancy is continuously increasing there.

If a stroke is survived, it usually leaves behind persistent damage, for example paralysis, speech disturbances and/or convulsions, which make it necessary for the patients to receive continuing intensive care with an enormous burden of suffering, also for the relatives, and an immense burden of costs on the health services. Thus, the cost for the treatment and aftercare of stroke patients in the USA alone is currently estimated at 20 billion U.S. dollars annually. In addition, approximately 10% of all surviving victims of stroke suffer another cerebrovascular accident during the first year thereafter, with a considerably worsened prognosis.

Hence the development and clinical establishment of an effective drug therapy which reduces both the acute mortality and the extent of the neurological deficits and the rate of recurrence, and thus distinctly improves the quality of life after a stroke, represent a huge challenge with social and medical significance for pharmaceutical research.

The cause of stroke is always a disturbance of the circulation, associated with oxygen deficiency, in a localized region of the brain. The signs and symptoms are characterized by disturbances of consciousness as far as coma, frequently spastic hemiplegia, symptoms of a wide variety of central motor and sensory deficits and focal or generalized convulsions. A distinction has to be made in the etiology between cerebral hemorrhage or encephalorrhagia, which is associated with high mortality (initial hemorrhagic insult; about 15% of cases; frequently as massive bleeding) after rupture of a vessel, mainly of the striolenticular arteries as a consequence of hypertension, arteriosclerosis or intracranial aneurysm as basic disorder, and cerebral infarct or encephalomalacia (initial non-hemorrhagic insult; about 85% of cases) with development of an ischemic focus of softening (necrosis) caused either by functional ischemia, inter alia as a result of a hypotensive crisis, usually of cardiac origin, or mainly due to progressive or persistent ischemia resulting from stenosing or obliterating vascular processes of arteriosclerotic, thrombotic and embolic origin in the region of the extra- and/or intracranial arteries, preferentially located in the internal carotid, middle cerebral and vertebral artery. The symptoms of encephalomalacia, which are rare and develop slowly, are referred to as "progressive stroke".

Preliminary signs that a cerebrovascular accident is threatening are regarded as being the frequently recurring transient ischemic attacks (TIA) lasting from 2 to 15 minutes with temporary symptoms of neurological deficit, whose origin is a transient, localized disturbance of blood flow caused by stenosis or by microembolisms, and which resolve within minutes to 24 hours at the most with complete recovery. Effective treatment of these ischemic attacks would therefore be very important for the prophylaxis of stroke.

Epidemiologically confirmed risk factors which favor the development of cerebral ischemias are, for example, arterial hypertension, hyperlipidemia, hyperuricemia, diabetes mellitus, rheological blood disorders, heart failure and the taking of hormonal contraceptives (Pschyrembel, Klinisches Wörterbuch [Chemical Dictionary], Walter de Gruyter-Verlag, 255th edition, 1986, page 1840).

The therapy currently applied to cerebrovascular disorders is confined to measures which have no direct effect on the cerebral ischemia (Schweiz. Med. Wochenschr. 1994, 124/45: 2005–2012). The only aim of the therapy is to maintain an adequate perfusion in the still intact area on the margin of the ischemic focus in order, at best, to limit the progressive infarction of the brain tissue. A predominant part is played, when the indication is appropriate, by vascular surgical procedures such as intramural desobliteration or the bridging of vascular stenoses by an extra/intracranial bypass, although these are associated with a relatively high operative risk. In particular, the medical procedures available at present do not permit causal treatment; on the contrary they are directed exclusively at eliminating the signs and symptoms. This includes primarily ensuring adequate cardiac function by administration of digitalis glycosides and antiarrhythmics, controlling the blood pressure, eliminating metabolic disturbances, mainly in the electrolyte and glucose balance, and preventing further thrombotic foci by antithrombotic therapy with acetylsalicylic acid or heparin, whereas anticoagulants of the vitamin K antagonist type (coumarins) are contraindicated because of the increased risk of hemorrhage. In addition, elimination of previously known risk factors is also thought to be of therapeutic importance.

Acute drug treatment of cerebral ischemia thus represents an as yet unsolved clinical problem (Ann. Radiol. 1994, 37/1–2: 132–135). This is also the conclusion of a recently published critical analysis of all the major clinical therapeutic studies carried out to date (Lancet 1992, 339/8792: 537–539), it being emphasized once again that reducing the mortality and limiting the neurological sequelae in the survivors are criteria of equal importance for assessing the result of treatment.

Clinicians are therefore demanding new therapeutic ideas aimed more at the causes. Promising approaches to this are provided by the complex pathophysiological processes at the vascular and cellular level which, in the form of a vicious circle, are at the basis of the progressive course of the acute cerebral ischemia. According to the current state of knowledge, the pathogenetic path from cellular ischemia and cell death is characterized by a cascade of physiological and biochemical processes involving a large number of mediator systems, which starts with deficient supply, consumption of high-energy compounds and collapse of energy metabolism, and leads, via excessive release of excitatory neurotransmitters, such as glutamate and aspartate, with limited or absent reuptake, to the pathological increase in concentration of intracellular calcium which is mainly responsible for the cytotoxicity. The fatal disturbance of calcium homeostasis goes hand in hand with other deleterious processes to contribute to the loss of cellular integrity. These include, inter alia, activation of membrane-associated phospholipases and the arachidonic acid metabolism, with formation of free fatty acids and their breakdown by the cyclooxygenase and lipoxygenase reaction pathways to prostaglandins and leukotrienes as mediators of inflammation, the production of aggressive oxygen free radicals with pronounced potential for damage to cell membranes, a drastic rise in membrane permeability, the development of vasogenic and cytotoxic cerebral edemas and the proteolysis, triggered by calcium ions, of protein structures intrinsic to the cell. Since all these mechanisms are time-dependent, there is a latency period between the occurrence of the ischemia and the death of cells of about 6 to a maximum of 12 hours, and medical interventions can have prospects of success only in this time window, if at all (Rev. Med. Interne 1994, 15/5: 350–356).

Attempts at new causal therapies are now concentrated on intervening specifically in the pathogenetic reaction cascade to interrupt, as soon as possible, the progressive course of the acute cerebral ischemia, and thus permanently to control the postischemic neuronal cell loss. At present, essentially two strategies are being followed (Stroke 1990, 21/8 Suppl. 1: 1-130–1-131); on the one hand, thrombolysis of thromboembolic and atherothrombotic blockages with fibrinolytics such as streptokinase, urokinase or recombinant tissue plasminogen activator r-tPA, with the aim of early rechannelization of the arterial system and, on the other hand, cytoprotection aimed at the survival of the neurons under ischemic conditions.

The neuroprotective therapeutic principles which have been intensively investigated, particularly by pharmacologists but, in some cases, also already by clinicians include, for example, suppression of the neuronal calcium influx with calcium antagonists (for example nimodipine, nicardipine, flunarizine and levemopamil), EAA (excitatory amino acid) antagonists (for example competitive and non-competitive NMDA (N-methyl-D-aspartate) and non-NMDA antagonists), or gangliosides (for example GM-1); blockade of the arachidonic acid cascade and elimination of its harmful metabolic products with phospholipase, cyclooxygenase and lipoxygenase inhibitors or PAF (platelet-activating factor), thromboxane and leukotriene antagonists; inhibition of the lipid peroxidation which damages cell membranes using oxygen free radical scavengers (for example superoxide dismutase, catalase, alpha-tocopherol, ascorbic acid, ginkgo leaves, allopurinol, tirilazad and melatonin) or heavy metal chelators (for example deferoxamine); limiting the spread of edema with anti-edematous active substances (for example corticosteroids); reducing the tendency to thrombosis with anticoagulants (for example heparin) and platelet aggregation inhibitors (for example ASA, ticlopidine, prostacycline and its more stable synthetic derivatives); and assisting endogenous protective factors with serotonin 1A agonists (for example urapidil and ipsapirone), adenosine modulators (for example propentofylline and vinpocetine) or neurotrophic growth factors (for example transforming growth factor TGF-β1 and brain-derived neurotrophic factor) and their release activators (Prog. Neuro-Psychopharmacol. Biol. Psychiatry 1993, 17/1: 21–70; Clin. Neuropharmacol. 1990, 13 Suppl 3: S9–S25). The greatest prospects of success in this are, of course, ascribed to a multifactorial intervention in the pathogenetic reaction cascade with its complex network of mutually amplifying mediator systems (Drugs 1988, 35/4: 468–476), whether by combining different selectively acting drugs or, more advantageously, by a single drug with the widest possible spectrum of pharmacological effects.

Besides propentofylline (3-methyl-1-(5-oxohexyl)-7-propylxanthine) which has already been mentioned, there have been investigations by pharmacologists to a greater or lesser extent and, in most cases, also by clinicians, of other xanthines, such as the methylxanthines theophylline (1,3-dimethylxanthine), theobromine (3,7-dimethylxanthine and caffeine (1,3,7-trimethylxanthine) which are widespread in nature, and the synthetic 1,3,7-trialkyl derivatives pentoxifylline (3,7-dimethyl-1-(5-oxohexyl)xanthine; Drugs & Aging 1995, 7/6: 480–503) and denbufylline (1,3-dibutyl-7-(2-oxopropyl)xanthine), without a clear therapeutic benefit having been detectable hitherto in the prophylaxis and treatment of acute ischemic stroke. On the contrary, the natural methylxanthines may in fact lead to a deterioration in the clinical situation (Schweiz. Rundsch. Med. Prax. 1989, 78/23: 663–666) and have therefore been said to be contraindicated. Only propentofylline appears to occupy a certain position as an exception, because of its exclusive profile of pharmacological effects, however (Gen. Pharmac. 1994, 25/6: 1053–1058; Drug. Dev. Res. 1993, 28/3: 438–444), although further controlled clinical studies with a sufficiently large number of patients are required in order to be able reliably to assess the therapeutic value of the product (J. Cereb. Blood. Flow Metab. 1993, 13/3: 526–530).

DETAILED DESCRIPTION OF THE INVENTION

It has now been found, surprisingly, that introduction of alkynol side chains with terminal amino functionality into position 1 and/or 7 of the xanthine framework results in compounds which, in clinically relevant experimental models, are distinctly superior to propentofylline and therefore have a greater therapeutic potential for the prophylaxis and treatment of cerebrovascular disorders.

The invention thus relates to novel xanthine compounds of the formula I, (I)

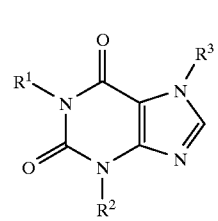

where
1) $R^1$ and $R^3$ are an alkynol residue of the formula Ia or Ib,

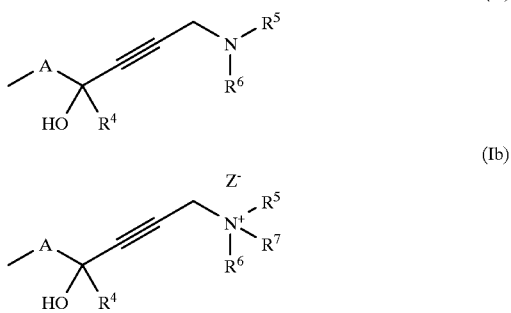

$R^2$ is
  a) straight-chain or branched $(C_1-C_5)$-alkyl,
  b) $(C_3-C_6)$-cycloalkyl or
  c) $(C_4-C_8)$-cycloalkylalkyl,
$R^4$ is a hydrogen atom or $(C_1-C_3)$-alkyl,
$R^5$, $R^6$ and $R^7$ are, independently of one another,
  a) a hydrogen atom,
  b) $(C_1-C_6)$-alkyl,
  c) $(C_3-C_6)$-cycloalkyl,
  d) $(C_4-C_8)$-cycloalkylalkyl,
  e) Ar-$(C_1-C_2)$-alkyl or
  f) tri-$(C_1-C_4)$-alkylsilyl, or
$R^5$ and $R^6$ form, together with the nitrogen atom to which they are bonded, a 4- to 7-membered saturated ring which is unsubstituted or substituted once to four times by $(C_1-C_4)$-alkyl, or
$R^5$ and $R^6$ form, together with the nitrogen atom to which they are bonded, a 4- to 7-membered saturated ring in which one ring -$CH_2$- group is replaced by a radical from the group of O, S, SO, $SO_2$ and $NR^{13}$, $R^{13}$ is a hydrogen atom, $(C_1-C_3)$-alkylcarbonyl or $(C_1-C_4)$-alkyl, and the ring is unsubstituted or substituted once to four times by $(C_1-C_4)$-alkyl,
A is unbranched or branched $(C_1-C_6)$-alkylene, and
$Z^-$ is the anion of a physiologically tolerated inorganic or organic acid, or
2) $R^1$ or $R^3$ is an alkynol residue of the formula Ia or Ib, and the other radical $R^3$ or $R^1$ is
  a) a hydrogen atom or
  b) $R^8$, in which $R^8$ is straight-chain or branched $(C_1-C_6)$-alkyl, $(C_3-C_6)$-cycloalkyl or $(C_4-C_8)$-cycloalkylalkyl,
and $R^2$, $R^4$, $R^5$, $R^6$, $R^7$, A and $Z^-$ are as defined under 1).

Preferred compounds of the formula I are those in which only one of the two radicals $R^1$ and $R^3$ is an alkynol residue of the formula Ia or Ib, and the other radical is a hydrogen atom or $R^8$.

Further preferred compounds of the formula I are those in which $R^1$ is an alkynol residue of the formula Ia or Ib and $R^3$ is a hydrogen atom or $R^8$.

Further preferred compounds of the formula I are those in which
$R^1$ is an alkynol residue of the formula Ia or Ib,
$R^2$ is straight-chain $(C_1-C_4)$-alkyl, cyclopropyl or cyclopropylmethyl,
$R^3$ is
  a) a hydrogen atom or b) $R^8$, in which $R^8$ is straight-chain or branched $(C_1-C_6)$-alkyl, cyclopropyl or cyclopropylmethyl,
$R^4$ is a hydrogen atom, methyl or ethyl, $R^5$, $R^6$ and $R^7$ are, independently of one another, a hydrogen atom, $(C_1-C_4)$-alkyl, cyclopropyl, cyclopropylmethyl or benzyl, or
$R^5$ and $R^6$ form, together with the nitrogen atom to which they are bonded, a 5- to 6-membered saturated ring from the group of morpholine, 4-$(C_1-C_3)$-alkylcarbonylpiperazine, 4-$(C_1-C_2)$-alkylpiperazine, piperazine, piperidine, pyrrolidine and thiomorpholine,
A is unbranched $(C_1-C_5)$-alkylene, and
$Z^-$ is the anion of a physiologically tolerated inorganic or organic acid.

Particularly preferred compounds of the formula I are those in which
$R^1$ is an alkynol residue of the formula Ia or Ib,
$R^2$ is $(C_1-C_4)$-alkyl,
$R^3$ is straight-chain $(C_2-C_4)$-alkyl or cyclopropyl,
$R^4$ is a hydrogen atom or methyl,
$R^5$, $R^6$ and $R^7$ are, independently of one another, a hydrogen atom, $(C_1-C_4)$-alkyl or benzyl, or
$R^5$ and $R^6$ form, together with the nitrogen atom to which they are bonded, the morpholine, pyrrolidine, piperidine, 4-methylpiperazine or 4-acetylpiperazine ring,
A is unbranched $(C_2-C_4)$-alkylene, and
$Z^-$ is the anion of a physiologically tolerated inorganic or organic acid.

Particularly preferred compounds are 1-(8-diethylamino-5-hydroxy-5-methyl-6-octynyl)-3-methyl-, 1-(5-hydroxy-5-methyl-8-pyrrolidino-6-octynyl)-3-methyl-, 3-butyl-1-(5-hydroxy-5-methyl-8-piperidino-6-octynyl)-, 1-(5-diethylamino-2-hydroxy-2-methyl-3-pentynyl)-3-propyl-, 1-(6-dimethylamino-3-hydroxy-3-methyl-4-hexynyl)-3-ethyl-, 1-(7-diethylamino-4-hydroxy-4-methyl-5-heptynyl)-3-ethyl-, 1-[8-(4-acetylpiperazino)-5-hydroxy-5-methyl-6-octynyl]-3-methyl-7-propylxanthine and their physiologically tolerated acid addition salts and N,N-diethyl-N-[4-hydroxy-4-methyl-8-(3-methyl-7-propyl-1-xanthinyl)-2-octynyl]-N-methylammonium iodide.

The term "$(C_4-C_8)$-cycloalkylalkyl" defines those alkyl radicals which are substituted by $(C_3-C_6)$-cycloalkyl with the total of all the carbon atoms being less than or equal to 8. These include, for example, cyclopropylmethyl to -pentyl, cyclobutylmethyl to -butyl, cyclopentylmethyl to -propyl and cyclohexylmethyl and -ethyl radicals. "Ar" designates radicals which are derived from benzene or naphthalene. Suitable 4- to 7-membered saturated rings for the structural element -$NR^5R^6$ are, for example, 4-$(C_1-C_4)$-alkylpiperazine, azetidine, 2,5-dimethylpyrrolidine, 2,6-dimethylpiperidine, morpholine, perhydroazepine (azepane), piperazine, piperidine, pyrrolidine, 2,2,6,6-tetramethylpiperidine, thiomorpholine and its sulfoxide or sulfone.

Suitable for forming the physiologically tolerated acid addition and quaternary ammonium salts of the formula I with the structural element of the formula Ib are, inter alia, hydrohalic acids such as hydrochloric, hydrobromic and hydroiodic acids, sulfuric, phosphoric, acetic, lactic, maleic, fumaric, oxalic, tartaric, citric, D-gluconic, 4-toluenesulfonic, methanesulfonic, benzenesulfonic and cyclohexylsulfamic acids or their particular anion $Z^-$.

The compounds of the formula I according to the invention always have a center of chirality, because of the secondary or tertiary alcohol structure in the alkynol residue of the formula Ia or Ib, and thus exist in enantiomeric forms. In addition, where the alkyl radical is asymmetrically branched in positions $R^2$ and/or $R^5$ to $R^8$ and/or where the alkylene group A is asymmetrically branched, further asymmetric carbons are present so that the compounds of the formula I now occur in diastereomeric forms. The invention therefore embraces not only all the stereoisomerically pure compounds, but also their mixtures.

The invention furthermore relates to a process for preparing the compounds of the formula I. In process variant A, a 3-alkylxanthine of the formual II,

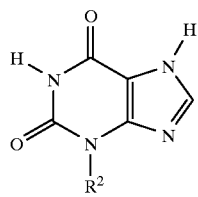
(II)

in which $R^2$ is as defined in formula I, is reacted, without condensing agent or in the presence of a basic condensing agent or of a salt of the compound of the formula II, with a compound of the formula III,

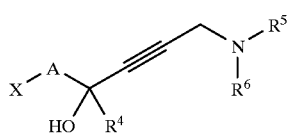
(III)

in which X is a halogen atom, preferably chlorine, bromine or iodine, or a sulfonic ester or phosphoric ester residue, and A, $R^4$, $R^5$ and $R^6$ are as defined in formula I, to give a compound of the formula Ic

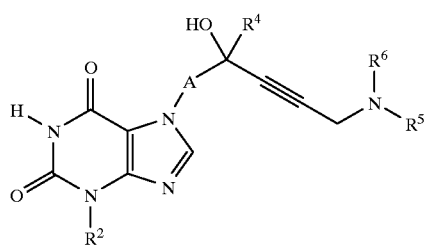
(Ic)

with an alkynol residue of the formula Ia for $R^3$ and a hydrogen atom for $R^1$ according to formula I, and subsequently alkylating the compound of the formula Ic without condensing agent or in the presence of a basic condensing agent or of a salt of the compound of the formula Ic either once again with a compound of the formula III to give a compound of the formula Id

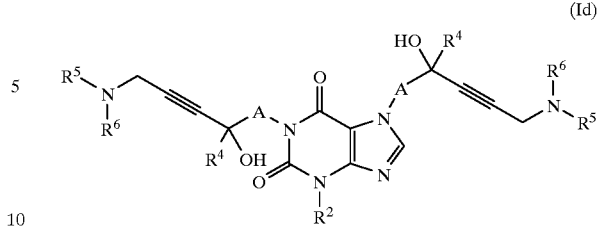
(Id)

with two identical or different alkynol residues of the formula Ia for $R^1$ and $R^3$ according to formula I or with a compound of the formula IV,

$R^8$-X (IV)

in which $R^8$ is as defined in formula I and X is as defined in formula III, to give a compound of the formula Ie

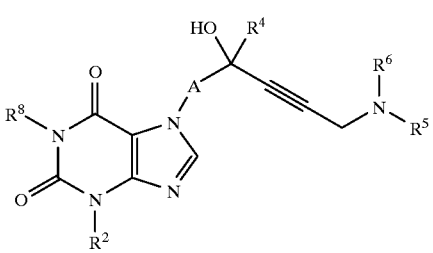
(Ie)

with the radical $R^8$ for $R^1$ and the alkynol residue of the formula Ia for $R^3$ according to formula I, or a 1,3-dialkylxanthine of the formula V,

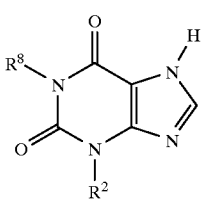
(V)

in which $R^2$ and $R^8$ are as defined in formula I, is reacted without condensing agent or in the presence of a basic condensing agent or else a salt of the compound of the formula V with a compound of the formula III to give a compound of the formula Ie, or a 3,7-dialkylxanthine of the formula VI,

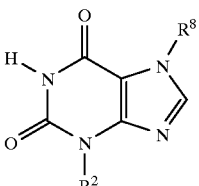
(VI)

in which $R^2$ and $R^8$ are as defined in formula I, is reacted without condensing agent or in the presence of a basic condensing agent or else a salt of the compound of the formula VI with a compound of the formula III to give a compound of the formula If

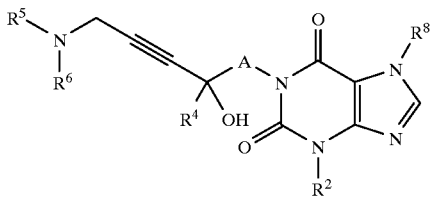
(If)

with an alkynol residue of the formula Ia for $R^1$ and the radical $R^8$ for $R^3$ according to formula I.

In process variant B, a compound of the formula II, V or VI is alkylated in analogy to process variant A with a compound of the formula VIII,

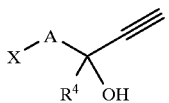
(VIII)

in which A and $R^4$ are as defined in formula I and X is as defined in formula III, to give a compound of the formula IX

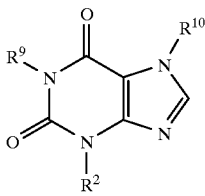
(IX)

in which either $R^9$ and $R^{10}$ are two identical or different radicals of the formula IXa

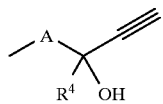
(IXa)

or else only $R^9$ or $R^{10}$ is a radical of the formula IXa, and the other radical $R^{10}$ or $R^9$ is a hydrogen atom or $R^8$, where $R^2$, A, $R^4$ and $R^8$ are as defined in formula I, and subsequently the compound of the formula IX is aminomethylated under the conditions of the Mannich reaction (RÖMPP Chemie Lexikon, 9th edition, Volume 4 (1991), page 2632) with formaldehyde and an amine of the formula X,

(X)

in which $R^5$ and $R^6$ are as defined in formula I, on the terminal ethynyl group(s) to give a compound of the formula Ic, Id, Ie or If.

In process variant C, a 1,3- or 3,7-di- or 1,3,7-trisubstituted xanthine of the formula XI,

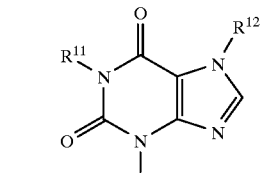
(XI)

in which either $R^{11}$ and $R^{12}$ are two identical or different radicals of the formula XIa

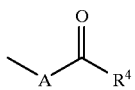
(XIa)

or else only $R^{11}$ or $R^{12}$ is a radical of the formula XIa, and the other radical $R^{12}$ or $R^{11}$ is a hydrogen atom or $R^8$, where $R^2$, A, $R^4$ and $R^8$ are as defined in formula I, is reacted with an organometallic compound of the formula XII,

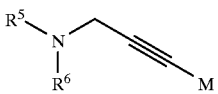
(XII)

in which $R^5$ and $R^6$ are as defined in formula I and M is an alkali metal such as sodium, potassium or, in particular, lithium; alkaline earth metal such as calcium or, in particular, magnesium, for example in the form of a Grignard compound (-Mg-halide); or heavy metal such as cerium, copper or silver; with reductive alkynylation of the carbonyl group(s) to give a compound of the formula Ic, Id, Ie, If or Ig

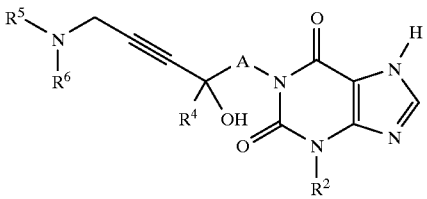
(Ig)

with an alkynol residue of the formula Ia for $R^1$ and a hydrogen atom for $R^3$ according to formula I.

In process variant D, a xanthine of the formula XI, in which $R^{11}$ and/or $R^{12}$ are the radical of the formula XIa is reacted in a reaction of the Nef type (RÖMPP Chemie Lexikon, 9th edition, Volume 4 (1991), page 2954) either with an acetylide of the formula XIII,

HC≡C-M (XIII)

in which M is as defined in formula XII, or else with a terminally protected acetylide of the formula XIV,

$R^a$-C≡C-M (XIV)

in which M is as defined in formula XII and $R^a$ is a leaving group which can subsequently be easily eliminated, for example the trimethylsilyl group (TMS) which can be eliminated with catalysis by fluoride, with ethynylation of the carbonyl group(s) to give a compound of the formula IX in which $R^9$ and/or $R^{10}$ are the radical of the formula IXa, and subsequently the resulting compound IX is aminomethylated by a Mannich reaction with formaldehyde and an amine of the formula X in analogy to process variant B to give a compound of the formula Ic, Id, Ie, If or Ig.

In process variant E, a compound of the formula Ic, Id, Ie or If prepared in process variants A to D, or a compound of the formula Ig prepared in process variants C or D, in which $R^5$ and/or $R^6$ are each a hydrogen atom, is reductively alkylated once or twice with an oxo derivative (aldehyde or ketone) of $(C_1–C_6)$alkanes, $(C_3–C_6)$ cycloalkanes, $(C_4–C_8)$ cycloalkylalkanes or Ar-$(C_1–C_2)$alkanes.

In process variant F, a compound prepared in process variants A to E is converted with a physiologically tolerated inorganic or organic acid HZ into an acid addition salt of the formula I, where $R^1$ and/or $R^3$ are the alkynol residue of the formula Ib, in which $R^7$ is a hydrogen atom and $R^2$ is as defined in formula I.

In process variant G, a compound prepared in process variants A to E is converted with an alkylating agent of the formula VII, $R^7$-Z  (VII)

where $R^7$ is as defined in formula I with the exception of hydrogen, and Z is as defined in formula III for X, into a quaternary ammonium salt of the formula I, where $R^1$ and/or $R^3$ are the alkynol residue of the formula Ib and $R^2$ is as defined in formula I.

In process variant H, a compound prepared in process variants A to G is fractionated into the pure stereoisomers by chromatography or by fractional crystallization.

The xanthines of the formula II, V, VI or XI, alkylating agents of the formula III, IV, VII or VIII; organometallic compounds of the formula XII, XIII or XIV and amines of the formula X used as starting materials in process variants A to D are known or can be prepared by known methods.

Thus, the alkynols of the formula III with basic substituents can be obtained, for example, by organometallic synthesis by reacting the sterically unhindered halo aldehydes or halo ketones of the formula Hal-A-CO-$R^4$ in a buildup reaction with reductive alkynylation of the carbonyl functionality with the 2-propynylamine metal compounds of the formula XII ($R^5R^6$N-$CH_2$-C≡C-M), preferably in the form of the lithium or halomagnesium (Grignard) compounds, under standard conditions (as described in detail hereinafter for process variants C and D). Similar reaction of the halo aldehydes and halo ketones with acetylides of the formula XIII (HC≡C-M) or XIV ($R^a$-C≡C-M) results, after elimination of the protective group $R^a$ on use of XIV, in the alkynols of the formula VIII.

The 2-propynylamines ($R^5R^6$N-$CH_2$-C≡CH) on which the organometallic compounds of the formula XII are based can be synthesized without difficulty from 2-propynyl bromide and the amines of the formula X by direct halogen/amine exchange or by the indirect route via the metal amides produced as intermediates in the following one-pot reaction which is disclosed in the literature (Tetrahedron 1992, 48/30: 6231–6244):

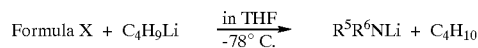

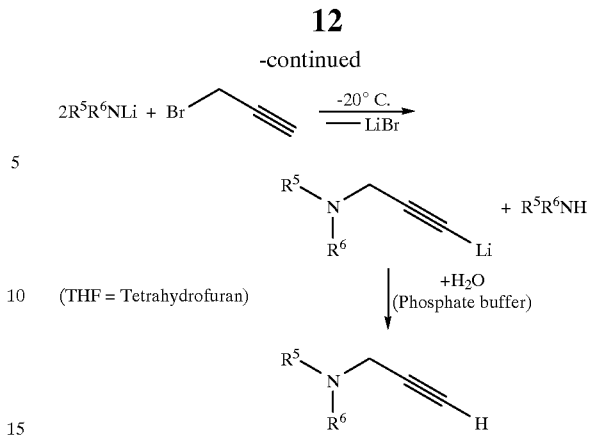

(THF = Tetrahydrofuran)

Reaction of the mono- and disubstituted xanthine derivatives II or Ic, Ig, V, VI and IX with the relevant reagents of the formula III, IV or VIII normally takes place in a dispersant or solvent which is inert towards the reactants. Particularly suitable ones are dipolar aprotic solvents, for example dimethylformamide, dimethylacetamide, N-methylpyrrolidone, tetramethylurea, hexamethylphosphoric triamide or dimethyl sulfoxide; however, it is also possible to use formamide, acetonitrile, acetone, butanone or alcohols such as methanol, ethylene glycol and its mono- and di$(C_1–C_4)$ alkyl ethers, ethanol, propanol, isopropanol and the various butanols; hydrocarbons such as benzene, toluene or xylenes; halogenated hydrocarbons such as dichloromethane or chloroform; pyridine and mixtures of said solvents or mixtures thereof with water.

The reaction is expediently carried out in the presence of a basic condensing agent. Suitable for this purpose are, for example, alkali metal or alkaline earth metal hydroxides, carbonates, hydrides, alcoholates and organic bases such as trialkylamines, for example triethyl- or tributylamine, quaternary ammonium or phosphonium hydroxides and crosslinked resins with attached, optionally substituted ammonium or phosphonium groups. However, the xanthine derivatives can also be employed directly in the form of their separately prepared salts, for example the alkali metal, alkaline earth metal or optionally substituted ammonium or phosphonium salts. Furthermore, the xanthine compounds can be alkylated without difficulty both in the presence of the abovementioned inorganic condensing agents and in the form of their alkali metal or alkaline earth metal salts with the assistance of phase transfer catalysts, for example tertiary amines, quaternary ammonium or phosphonium salts or else crown ethers, preferably in a two-phase system under the conditions of phase transfer catalysis. Suitable phase transfer catalysts, most of which are commercially available, are, inter alia, tetra-$(C_1–C_4)$-alkyl- and methyltrioctylammonium and -phosphonium, methyl-, myristyl-, phenyl- and benzyl-tri-$(C_1–C_4)$-alkyl- and cetyltrimethylammonium or $(C_1–C_{12})$-alkyl- and benzyltriphenylphosphonium salts, the compounds which prove more effective being, as a rule, those having the larger cation of more symmetric structure.

The reaction temperatures for this are generally between 0° C. and the boiling point of the reaction medium used in each case, preferably between 20° C. and 130° C., where appropriate under elevated or reduced pressure, but usually under atmospheric pressure, in which case the reaction time can be from less than one hour up to several hours.

The optional reductive alkylation of compounds of the formulae Ic to Ig with terminal primary ($R^5$ and $R^6$=H) or secondary ($R^5$ or $R^6$=H) amino group in the alkynol side chain to give secondary or tertiary amines takes place by reaction with one of the oxo derivatives (aldehydes or ketones), which are all known from the literature, of ($C_1$–$C_6$) alkanes, ($C_3$–$C_6$)cycloalkanes, ($C_4$–$C_8$)cycloalkylalkanes or Ar($C_1$–$C_2$)alkanes in the presence of a suitable reducing agent. The azomethines which are formed as intermediates from oxo compound and amine are reduced, for example, with formic acid and derivatives thereof; however, hydrogenation with complex metal hydrides such as lithium alanate, lithium or sodium boranate and, in particular, sodium cyanoboranate, is preferred. This is expediently carried out in a dispersant or solvent which is inert towards the reactants, for example an ether such as diethyl ether, dioxane or tetrahydrofuran; a lower alcohol, preferably methanol or ethanol; water or mixtures thereof with one another at temperatures between 20° C. and the boiling point of the reaction mixture.

Conversion of the xanthine Ic to Ig with the acids HZ into the physiologically tolerated acid addition salts may be carried out using methods well known in the art. The preparation of the physiologically tolerated quaternary ammonium salts from the xanthines Ic to Ig by alkylation with the reagents of the formula VII, preferably in the form of alkyl halides ($R^7$Hal), in particular the iodides $R^7$I, or dialkyl sulfates ($R^7_2SO_4$), is expediently carried out in inert dispersions or solvents such as di($C_1$–$C_4$)alkyl ethers, cyclic ethers, aromatic or halogenated hydrocarbons or ketones (for example acetone), or else in mixtures of these solvents or with addition of dipolar aprotic solvents (for example dimethylformamide) at temperatures from 20° C. to the boiling point of the relevant reaction medium, several hours frequently being needed until the reaction is complete. This usually results in the quaternary salts in crystalline form. If required, their anion $Z^-$ can subsequently be varied as required with the aid of anion exchangers.

The Mannich three-component condensation for aminomethylation (Weygand/Hilgetag: Organisch-chemische Experimentierkunst, [Experiments in organic chemistry] 4th edition, 1970, pages 990–993) of compound IX at the terminal acetylene group with acidic CH can in principle be carried out with ammonia, primary or, preferably, secondary amines of the formula X in the presence of formaldehyde as carbonyl component (employed either in aqueous solution or, advantageously, in solid form as paraformaldehyde) under the catalytic influence both of bases and of acids. However, the acid-catalyzed process is preferred, in which the amines X are reacted in the form of their salts, for example the hydrochlorides or acetates. It is often appropriate to add catalytic amounts of metal salts such as, for example, zinc(II), iron(III) or, in particular, copper(I) chloride (J. Med. Chem. 1990, 33: 3182–3189).

In general, lower alcohols, di-($C_1$–$C_4$)alkyl ethers or, preferably, cyclic ethers, especially dioxane, are used as reaction medium. The reaction temperature is usually between 20° C. and the boiling point of the reaction mixture, preferably between 30° C. and 70° C., with reaction times of up to several hours being usual.

The 3-alkylated mono- or dioxoalkylxanthines of the formula XI which are employed as starting materials in the organometallic reactions in process variants C and D are mostly known, inter alia from U.S. Pat. No. 4,289,776 and U.S. Pat. No. 4,242,345, or can easily be prepared from the mono- or dialkylxanthines of the formula II and V or VI and the halo aldehydes or halo ketones of the formula Hal-A-CO-$R^4$, where appropriate also in the form of their open-chain or cyclic acetals or ketals, under the alkylation conditions which have been described in detail hereinbefore. Moreover, those compounds XI which have a hydrogen atom in the position of $R^{12}$ and an oxalkyl radical of the formula XIa and the position of $R^{11}$ can be obtained without difficulty by the alternative route via 1-oxoalkyl-3,7-dialkylxanthines in which the alkyl radical in position 7 is a leaving group which can easily be eliminated, for example in the form of the benzyl group which can be removed by reduction or the meth-, eth-, prop- or butoxymethyl radical which can be eliminated by hydrolysis, by the method described in detail in WO 87/00523.

Among the organometallic compounds of the formula XII, XIII or XIV suitable for alkynylation of the carbonyl groups, the lithium and halomagnesium (Grignard) derivatives occupy a preferred position because they are easy to obtain and manipulate. Thus, the 2-propynylamines of the formula $R^5R^6$ N-$CH_2$-C≡CH described hereinbefore, and the acetylenes of the formula $R^a$-C≡CH which are protected at one end, preferably ethynyltrimethylsilane, can be metallated with ($C_1$–$C_4$)alkyllithium compounds, preferably butyllithium, in one of the solvents listed hereinafter, mainly anhydrous tetrahydrofuran, at low temperatures between –50° C. and –80° C. or with ($C_1$–$C_4$)alkylmagnesium halides, for example methyl- or ethylmagnesium chloride or bromide, in a low-boiling ether, as a rule diethyl ether, at the boiling point, quantitatively to give compounds of the formula XII or XIV, which are reacted without intermediate isolation with the carbonyl compounds XI. It is possible and advantageous to employ as reagent of the formula XIII commercially obtainable lithium acetylide in the form of the stable ethylenediamine complex, and addition of dry cerium (III) chloride in at least the stoichiometric amount is recommended to increase the reactivity (Tetrahedron Letters 1984, 25/38: 4233–4236). The highly nucleophilic organometallic compounds are very sensitive to hydrolysis and oxidation; safe handling thereof therefore requires rigorous exclusion of moisture and, where appropriate, use of a protective gas atmosphere.

The usual solvents or dispersants for the alkynylation reaction are mainly those which are also suitable for preparing the organometallic compounds. Particularly suitable as such are ethers with one or more ether oxygen atoms, for example diethyl, dipropyl, diisopropyl or dibutyl ether, 1,2-dimethoxyethane, tetrahydrofuran, dioxane, tetrahydropyran, furan and anisole, and aliphatic or aromatic hydrocarbons such as petroleum ether, cyclohexane, benzene, toluene, xylenes, diethylbenzenes and tetrahydronaphthalene; however, it is also possible to use tertiary amines such as triethylamine, or dipolar aprotic solvents, for example dimethylformamide, dimethylacetamide, N-methylpyrrolidone, hexamethylphosphoric triamide and dimethyl sulfoxide, and mixtures of said solvents.

The alkynylation reaction is, as a rule, carried out at temperatures between –40° C. and +100° C., preferably between –20° C. and +70° C. or at room temperature without external cooling, with the particular organometallic compound normally being used in slight excess. The reaction times usually extend from a few minutes up to several hours. The alcoholates which are formed are preferably decomposed with water, aqueous ammonium chloride solution or dilute hydrochloric or acetic acid.

The desilylation both of the alkynols protected on the ethynyl moiety and obtained from the carbonyl compounds XI by reaction with lithium trimethylsilylacetylide (XIV) to give the intermediate compounds of the formula IX, and of the compounds of the formula I according to the invention with N-trialkylsilylated alkynol side chains can advantageously be carried out by methanolysis in the presence of catalytic amounts of potassium fluoride, which takes place quantitatively within a few hours at temperatures between 20° C. and the boiling point of the methanol.

Compounds I according to the invention can be prepared in stereoisomerically pure form either by starting from sterically homogeneous starting materials of the formula III or VIII (where appropriate also II, IV, V, VI, VII, X and/or XI) and intermediate compounds of the formula IX, or in process variants C and D by designing the alkynol formation from the prochiral carbonyl compounds XI with the organometallic compounds XII, XIII or XIV to be enantioselective by asymmetric induction in the presence of chiral auxiliaries.

However, it is preferred for the stereoisomeric forms to be separated subsequently by methods known per se. Since diastereomers have, in contrast to enantiomers, different physical and chemical properties, as a rule there are no difficulties in separating mixtures thereof, for example by fractional crystallization or by chromatographic processes. By contrast, physical racemate resolution into the enantiomeric forms (antipodes) requires additional measures; thus, fractional crystallization is possible only after formation of diastereomeric salts with an optically active acid HZ and chromatographic separation is preferably only on use of chiral stationary phases which show different spatial affinity for the enantiomers.

The alkynols of the formula IX not only are valuable intermediates for synthesizing the compounds of the formula I according to the invention, but, in addition, themselves show the same type of pharmacological effects as the final products of the formula I, although they are less soluble in water.

The compounds of the formula I are suitable, because of their valuable pharmacological properties, in an outstanding manner for use as active substances in pharmaceuticals, in particular in those which permit effective curative and prophylactic treatment of cerebrovascular disorders caused by ischemia, such as stroke; transient ischemic attacks (TIA); multiinfarct dementia; dementia of the mixed type with vascular and degenerative (Alzheimer) components; spinal cord damage; brain trauma as a result of head injuries; and neuronal damage after cardiac arrest, (neonatal) asphyxia and resuscitation, and vascular surgical operations (for example bypass operations) in the region of the main arteries supplying the brain. It is moreover possible for the compounds of the formula I to be administered either on their own, for example in the form of microcapsules, in mixtures with one another or in combination with suitable excipients.

A compound of formula I, while effective itself, may be formulated and administered in the form of its pharmaceutically acceptable acid addition salt for purposes of stability, convenience of crystallization, increased solubility and the like. In addition, an individual polymorph, solvate or individual optical isomer of a compound of formula I may be used.

As used herein, the term "curative" refers to a decrease in symptom severity over that expected in the absence of treatment and does not necessarily indicate a total elimination or cure of the cerebrovascular disorder.

As used herein, the term "therapeutically effective amount" means an amount of the compound which is effective in treating the named disorder. A therapeutically effective amount can be readily determined by the attending diagnostician, as one skilled in the art, by the use of known techniques and by observing results obtained under analogous circumstances.

As used herein, the term "patient" refers to a mammal such as a dog, cat, guinea pig, mouse, rat or human being.

The terms "treating" or "to treat" means to alleviate symptoms, eliminate the causation either on a temporary or permanent basis, or to prevent or slow the appearance of symptoms of the named disorder.

The present invention relates, on the one hand, to the use of the pharmaceuticals according to the invention in all types of therapy currently practiced for cerebrovascular disorders (Schweiz. Med. Wochenschr. 1994, 124/45: 2005–2012), such as primary prevention for suppressing the threat of ischemic attacks, acute treatment to limit the infarction of the tissue after onset of ischemia and secondary prophylaxis to reduce the rate of recurrence after an ischemic episode and, on the other hand, to the use of the pharmaceuticals in the form of pharmaceutical compositions, in particular for parenteral and oral, but also rectal or transdermal where appropriate, administration.

The present invention provides a method of treating a patient suffering from a cerebrovascular disorder. The identification of those patients who would benefit from the present invention is well within the ability and knowledge of one skilled in the art. A clinician skilled in the art can readily identify, by the use of clinical tests, physical examination and medical/family history, those patients who are suffering from a cerebrovascular disorder.

The present invention also provides a pharmaceutical composition comprising at least one compound of the formula I as active substance. The pharmaceutical composition can be administered according to the present invention in any suitable form or mode which makes the compound bioavailable in effective amounts. One skilled in the art of preparing formulations can readily select the proper form and mode of administration depending upon the particular characteristics of the compound selected, the disease state to be treated, the stage of the disease, and other relevant circumstances.

Suitable solid or liquid pharmaceutical forms are, for example, granules, powders, tablets, coated tablets, (micro) capsules, syrups, emulsions, suspensions, gels, products with protracted release of active substance, suppositories, plasters which release the active substance, aerosols, drops and, in particular, injectible solutions in the form of ampoules or injection bottles for continuous infusion, in the production of which auxiliaries such as excipients, disintegrants, binders, coating agents, swelling agents, glidants or lubricants, flavorings, sweeteners or solubilizers are normally used. Examples of auxiliaries which are frequently used and which may be mentioned are magnesium carbonate, titanium dioxide, lactose, mannitol and other sugars, talc, lactose, gelatin, starch, vitamins, cellulose and its derivatives, animal and vegetable oils, polyethylene glycols and solvents such as, for example, sterile water, physiological saline, alcohols, glycerol and other polyhydric alcohols (polyols).

The pharmaceutical products are preferably produced and administered in dosage units, each unit containing as active ingredient a particular dose of the compound of the formula I. In the case of solid dosage units such as tablets, capsules and suppositories, this dose can be up to 1000 mg, but preferably 100 to 600 mg, and in the case of injection solutions in ampoule form up to 300 mg, but preferably 20 to 200 mg.

The daily dosages indicated for treating an adult patient are, depending on the activity of the compounds of the formula I in humans and the severity of the life-threatening disorder, from 100 to 5000 mg of active substance, preferably 300 to 3000 mg, on oral administration and from 30 to 3000 mg, preferably 50 to 2000 mg, on intravenous administration. The daily dose can be administered either by a single administration in the form of a single dosage unit or as a plurality of smaller dosage units and by multiple administration of divided doses at particular intervals of time. The daily dose on continuous intravenous infusion is 100 to 5000 mg, preferably 500 to 2000 mg, corresponding to an infusion rate of from 0.1 to 3 mg per kg of body weight and hour (h), preferably from 0.3 to 1 mg/kg/h. However, in certain circumstances, higher or lower daily doses may also be appropriate with all administration forms.

The compounds of the formula I can also be administered with other suitable active substances, in particular with those which likewise intervene to control the pathogenetic reaction cascade of acute cerebral ischemia; for example with fibrinolytics, calcium antagonists, EAA (excitatory amino acids) antagonists, gangliosides, phospholipase, cyclooxygenase and lipoxygenase inhibitors, PAF (platelet-activating factor), thromboxane and leukotriene antagonists, oxygen free radical scavengers, heavy metal chelators, antiedematous active substances, anticoagulants, platelet application inhibitors, serotonin 1A agonists, adenosine modulators and neurotrophic growth factors and their release activators; or be formulated together with them in the production of the pharmaceutical forms.

The disclosures of German application serial no. 19622734.8 filed Jun. 7, 1996 and German application serial no.19636882.0 filed Sep. 11, 1996 are herein incorporated by reference.

The synthesis of the compounds of the formula I which are summarized by structural aspects in Table 1 is explained in detail hereinafter by means of representative preparation examples. Table 2 is a compilation of the compounds of the formula IX. The structure of all the intermediates and final products produced by preparation was verified both by $^1$H-NMR spectroscopy and by elemental analysis or mass spectrum.

EXAMPLE 1

1-(8-Diethylamino-5-hydroxy-5-methyl-6-octynyl)-3-methyl-7-propylxanthine hydrochloride by process variants D and F:

D1) 1-(5-Hydroxy-5-methyl-6-heptynyl)-3-methyl-7-propylxanthine

A solution of 153.2 g (0.5 mol) of 3-methyl-1-(5-oxohexyl)-7-propylxanthine in 750 ml of dioxane was added dropwise to a suspension of 75.5 g (0.82 mol) of lithium acetylide as ethylenediamine complex in 500 ml of dioxane with exclusion of moisture and stirring at room temperature. The slightly exothermic reaction which started during this was completed by stirring and heating at 70° C. for 6 hours. Subsequently, at room temperature, water was added, the organic solvent was distilled off as far as possible under reduced pressure, the aqueous phase was exhaustively extracted with chloroform, the extract was dried over sodium sulfate and then concentrated under reduced pressure, and the residue was purified by filtration through a silica gel column in chloroform as eluent, resulting in 150.4 g (91% of theory) of oily product which gradually solidified and was recrystallizable from ethyl acetate with the addition of petroleum ether at the boiling point.

Yield: 136.8 g (82% of theory); melting point: 98° C.
$C_{17}H_{24}N_4O_3$ (MW=332.41 g/mol)
Analysis: Calculated: C 61.42% H 7.28% N 16.86%
Found: C 61.48% H 7.37% N 16.68%

D2) 1-(8-Diethylamino-5-hydroxy-5-methyl-6-octynyl)-3-methyl-7-propylxanthine 16.6 g (50 mmol) of the intermediate compound from stage D1), 1.8 g (60 mmol) of paraformaldehyde, 7.3 g (0.1 mol) of diethylamine and 0.8 g of zinc (II) chloride were stirred under reflux in 250 ml of dry dioxane for 5 hours. The solvent was then distilled off under reduced pressure, and the reddish oily residue was purified by filtration through a silica gel column in chloroform/methanol (19:1) as eluent.

Yield: 12.6 g (60% of theory); pale yellow oil
$C_{22}H_{35}N_5O_3$ (MW=417.56 g/mol)

F3) 1-(8-Diethylamino-5-hydroxy-5-methyl-6-octynyl)-3-methyl-7-propylxanthine hydrochloride For salt formation, the 12.6 g (30 mmol) of base from stage D2) were dissolved in 30 ml of 1 N hydrochloric acid and evaporated to dryness under reduced pressure, the solid residue was dried under oil pump vacuum overnight and taken up in hot ethanol, the solution was decolorized with active carbon and filtered hot, and diisopropyl ether was added at the boiling point until cloudy, and the hydrochloride was left to crystallize out with cooling.

Yield: 11.5 g (84% of theory); melting point: 132° C.
$C_{22}H_{36}ClN_5O_3$ (MW=454.03 g/mol)
Analysis: Calculated: C 58.20% H 7.99% Cl 7.81% N 15.43%
Found: C 58.12% H 8.24% Cl 7.84% N 15.37% by process variants C and F:

C1) N,N-Diethyl-2-propynylamine

A mixture of 100 ml (0.16 mol) of a 1.6 M solution of n-butyllithium in n-hexane and 100 ml of tetrahydrofuran was cooled to −78° C. with stirring and, at this temperature, 11.7 g (0.16 mol) of diethylamine were added dropwise; the mixture was subsequently allowed to reach room temperature, was stirred for one hour and was again cooled to −20° C., and a solution of 9.04 g (76 mmol) of 2-propynyl bromide in 50 ml of tetrahydrofuran was added dropwise. The reaction mixture was left to stand at room temperature overnight, then stirred into cold aqueous phosphate buffer solution and exhaustively extracted with chloroform, the extract was dried over sodium carbonate and concentrated, and the residue was fractionally distilled through a column.

Yield: 6.2 g (73% of theory); boiling point: 117° C. (literature: 119° C.)
$C_7H_{13}N$ (MW=111.19 g/mol)

C2) 1-(8-Diethylamino-5-hydroxy-5-methyl-6-octynyl)-3-methyl-7-propylxanthine 32.4 ml (52 mmol) of a 1.6 M solution of n-butyllithium in n-hexane was added dropwise in 30 minutes to 5.8 g (52 mmol) of N,N-diethyl-2-propynylamine from stage C1) dissolved in 40 ml of tetrahydrofuran at between −60° C. and −65° C. The mixture was stirred at −70° C. for one hour and then warmed to room temperature, and a solution of 12.3 g (40 mmol) of 3-methyl-1-(5-oxohexyl)-7-propylxanthine in 60 ml of tetrahydrofuran was added dropwise over the course of 20 minutes, during which the temperature of the reaction mixture rose to 35° C. After stirring at room temperature for four hours, 100 ml of cold 1 N hydrochloric acid were added, the mixture was extracted by shaking several times with dichloromethane, the aqueous phase was made alkaline with sodium carbonate, the reaction product was extracted with dichloromethane, and drying of the sodium sulfate was followed by concentration under reduced pressure. The oily residue was purified by filtration through a silica gel column in chloroform/methanol (19:1) as eluent.

Yield: 13.9 g (83% of theory); colorless oil
$C_{22}H_{35}N_5O_3$ (MW=417.56 g/mol)

F3) 1-(8-Diethylamino-5-hydroxy-5-methyl-6-octynyl)-3-methyl-7-propylxanthine hydrochloride Conversion of the 13.9 g (33.3 mmol) of base from stage C2) into the hydrochloride took place as described for process variant D, although it was possible to dispense with the use of active carbon in the recrystallization from ethanol/diisopropyl ether.

Yield: 13.8 g (91% of theory); melting point: 132° C.

$C_{22}H_{36}ClN_5O_3$ (MW=454.03 g/mol)

Analysis: Calculated: C 58.20% H 7.99% Cl 7.81% N 15.43%

Found: C 58.02% H 8.26% Cl 7.94% N 15.27% by process variants B and F:

B1) 1-Chloro-5-hydroxy-5-methyl-6-heptyne 200 g (2.17 mol) of lithium acetylide in the form of the ethylenediamine complex were suspended in 800 ml of dry dioxane and, while stirring vigorously and cooling in ice, 269.2 g (2.0 mol) of 1-chloro-5-hexanone were rapidly added dropwise, during which the temperature rose to 48° C. The exothermic reaction was allowed to subside while stirring for 3 hours without further external cooling, 500 ml of water were cautiously added, the mixture was filtered, most of the dioxane was distilled off under reduced pressure, the aqueous phase was extracted exhaustively with chloroform, the extract was dried over sodium sulfate, the solvent was evaporated off under reduced pressure, and the residue was subjected to fractional distillation.

Yield: 190.2 g (59% of theory); boiling point (8 mbar): 87–88° C.

$C_8H_{13}ClO$ (MW=160.65 g/mol)

B2) 1-(5-Hydroxy-5-methyl-6-heptynyl)-3-methyl-7-propylxanthine

The mixture of 6.25 g (30 mmol) of 3-methyl-7-propylxanthine, 4.8 g (30 mmol) of the chloroalkynol from stage B1) and 4.15 g (30 mmol) of potassium carbonate in 150 ml of dimethylformamide was stirred at 130° C. for 3 hours, then filtered hot and concentrated under reduced pressure. The residue was taken up in chloroform, washed first with 1 N sodium hydroxide solution and then with water to neutrality, and dried over sodium sulfate, the solvent was distilled off under reduced pressure, and the product was recrystallized from ethyl acetate with the addition of petroleum ether at the boiling point.

Yield: 3.6 g (36% of theory); melting point: 98° C.

$C_{17}H_{24}N_4O_3$ (MW=332.41 g/mol)

Analysis: Calculated: C 61.42% H 7.28% N 16.86%

Found: C 61.63% H 7.41% N 16.87%

This intermediate compound is identical to the product of Example 1D1) and was converted by Mannich reaction with paraformaldehyde and diethylamine and salt formation (Examples 1D2) and 1F3)) to the final product.

by process variants A and F:

A1) 1-Chloro-8-diethylamino-5-hydroxy-5-methyl-6-octyne 12.37 ml (19.8 mmol) of a 1.6 M solution of n-butyllithium in n-hexane were slowly added dropwise to a solution of 2.0 g (18 mmol) of N,N-diethyl-2-propynylamine (Example 1C1)) in 50 ml of tetrahydrofuran at −78° C. After one hour at −78° C., the mixture was warmed to room temperature, and 2.42 g (18 mmol) of 1-chloro-5-hexanone were added. Stirring at room temperature for one hour was followed by adjustment to pH 7 with 2 N hydrochloric acid and partitioning between 5% strength sodium bicarbonate solution and dichloromethane. The organic phase was dried over magnesium sulfate, the solvent was removed under reduced pressure. Yield: 4.38 (99% of theory); oily product $C_{13}H_{24}ClNO$ (MW=245.83 g/mol); $^1$H-NMR (DMSO-$d_6$, 200 MHz): δ=0.97 (t, 6 H, N(CH$_2$CH$_3$)$_2$); 1.33 (s, 3 H, CH$_3$); 1.40–1.85 (m, 6 H, CH$_2$); 2.45 (q, 4 H, N(CH$_2$CH$_3$)$_2$); 3.33 (s, 2 H, NCH$_2$C≡C); 3.63 (t, 2 H, CH$_2$Cl); 5.12 (s, 1 H, OH)

It was possible to employ the substance without further purification directly in the alkylation reaction in stage A2).

A2) 1-(8-Diethylamino-5-hydroxy-5-methyl-6-octynyl)-3-methyl-7-propylxanthine 2.12 g (15.3 mmol) of potassium carbonate were added to a solution of 2.0 g (9.6 mmol) of 3-methyl-7-propylxanthine in 60 ml of dimethylformamide at 60° C. and the mixture was stirred at 60° C. for one hour. Then 3.07 g (12.5 mmol) of 1-chloro-8-diethylamino-5-hydroxy-5-methyl-6-octyne from stage A1) were added dropwise and the mixture was stirred at 80° C. for 12.5 hours. It was then allowed to cool to room temperature, water was added, and three extractions with tert-butyl methyl ether were carried out. The organic phase was dried over magnesium sulfate, concentrated under reduced pressure and purified by flash chromatography, dichloromethane/methanol=19/1.

Yield: 2.29 g (57% of theory); yellowish oil $C_{22}H_{35}N_5O_3$ (MW=417.56 g/mol)

The substance was identical to the products prepared in Example 1D2) and 1C2) and was converted into the hydrochloride in analogy to Example 1F3).

EXAMPLE 1a (+)-1-(8-Diethylamino-5-hydroxy-5-methyl-6-octynyl)-3-methyl-7-propylxanthine hydrochloride

EXAMPLE 1b (−)-1-(8-Diethylamino-5-hydroxy-5-methyl-6-octynyl)-3-methyl-7-propylxanthine hydrochloride by process variants H and F:

The racemic 1-(8-diethylamino-5-hydroxy-5-methyl-6-octynyl)-3-methyl-7-propylxanthine hydrochloride prepared by process variants A, B, C or D and F in Example 1 was separated into the enantiomerically pure bases by high pressure liquid chromatography (HPLC) on a column (250× 4.6 mm) with chiral support material (CSP Chiralpak AD) in the eluent n-hexane/2-propanol (85+15) with the addition of 0.1% diethylamine.

$C_{22}H_{35}N_5O_3$ (MW=417.56 g/mol)

(+)-Enantiomer: Retention time 11.61 minutes; optical purity 100%

(−)-Enantiomer: Retention time 14.46 minutes; optical purity 100%

The enantiomeric bases were converted into the hydrochloride as in Example 1F3) by process variant C.

$C_{22}H_{36}ClN_5O_3$ (MW=454.03 g/mol)

(+) Enantiomer 1a: Yield 82%; melting point 86° C.

(−) Enantiomer 1b: Yield 70%; melting point 89° C.

EXAMPLE 2

N,N-Diethyl-N-[4-hydroxy-4-methyl-8-(3-methyl-7-propyl-xanthin-1-yl)-2-octynyl]-N-methylammonium iodide (by process variant G)

1 g (2.4 mmol) of 1-(8-diethylamino-5-hydroxy-5-methyl-6-octynyl)-3-methyl-7-propylxanthine—prepared as in Example 1A2), 1C2) or 1D2)—was introduced into 30 ml of diethyl ether, 425 mg (3.0 mmol) of methyl iodide were added, and the mixture was stirred at room temperature for 20 hours. Then a further 212 mg (1.5 mmol) of methyl iodide were added and the mixture was stirred under reflux for 2 hours. The resulting crystals were filtered off with suction, washed with diethyl ether and dried.

Yield: 813 mg (60% of theory); melting point: 160° C.

$C_{23}H_{38}IN_5O_3$ (MW=559.51 g/mol); mass spectrum: 432 (100%, M$^+$)

EXAMPLE 3

1-(6-Dimethylamino-3-hydroxy-3-methyl-4-hexynyl)-3-methyl-7-propylxanthine fumarate by process variants C and F:

C1) 1-(6-Dimethylamino-3-hydroxy-3-methyl-4-hexynyl)-3-methyl-7-propylxanthine 4.32 g (52 mmol) of N,N-dimethyl-2-propynylamine, 32.4 ml (52 mmol) of n-butyllithium as 1.6 M solution in n-hexane and 11.1 g (40 mmol) of 3-methyl-1-(3-oxobutyl)-7-propylxanthine were reacted in tetrahydrofuran and worked up in analogy to Example 1C2), but using chloroform in place of dichloromethane as extractant.

Yield: 13.2 g (91% of theory); oily product
$C_{18}H_{27}N_5O_3$ (MW=361.45 g/mol)

F2) 1-(6-Dimethylamino-3-hydroxy-3-methyl-4-hexynyl)-3-methyl-7-propylxanthine fumarate To convert the base into the fumarate, the 13.2 g (36.5 mmol) of oily substance from stage C1) were taken up in 50 ml of ethanol, and a hot solution of 4.24 g (36.5 mmol) of fumaric acid in 100 ml of ethanol was added. The solution was subsequently concentrated to incipient cloudiness, boiled and left for crystallization of the salt.

Yield: 14.1 g (81% of theory); melting point: 170° C.
$C_{22}H_{31}N_5O_7$ (MW=477.53 g/mol)

by process variants D and F:

D1) 1-(3-Hydroxy-3-methyl-4-pentynyl)-3-methyl-7-propylxanthine

A solution of 55.7 g (0.2 mol) of 3-methyl-1-(3-oxobutyl)-7-propylxanthine in a mixture of 200 ml each of dioxane and toluene was added dropwise in 45 minutes to a stirred suspension of 36.8 g (0.4 mol) of lithium acetylide as ethylenediamine complex and 98.6 g (0.4 mol) of anhydrous cerium(III) chloride in a mixture of 500 ml each of dry dioxane and toluene at 50° C. The mixture was then stirred at 50° C. for 7 hours, cooled and, after addition of cold water and acidification with 2 N hydrochloric acid, intensively extracted with chloroform, the extract was washed with water, dried over sodium sulfate and evaporated under reduced pressure, and the residue was purified by filtration through a silica gel column in the eluent chloroform/methanol (50:1), resulting in 35.0 g (58% of theory) of solid, which was recrystallized from ethanol with large losses.

Yield: 18.0 g (30% of theory); melting point: 149° C.
$C_{15}H_{20}N_4O_3$ (MW=304.36 g/mol)
Analysis: Calculated: C 59.20% H 6.62% N 18.41%
Found: C 58.72% H 6.51% N 18.33%

This intermediate compound was converted into the final product by Mannich reaction with paraformaldehyde and dimethylamine hydrochloride in analogy to Example 1D2) and subsequent salt formation as in Example 3F2).

EXAMPLE 4

1-(5-Hydroxy-5-methyl-8-pyrrolidino-6-octynyl)-3-methyl-7-propylxanthine fumarate (by process variant B or D and F)

A mixture of 9.97 g (30 mmol) of the intermediate compound 1-(5-hydroxy-5-methyl-6-heptynyl)-3-methyl-7-propylxanthine from Example 1D1), or prepared as in Example 1B2), 1.02 g (34 mmol) of paraformaldehyde, 2.05 g (34 mmol) of glacial acetic acid, 2.42 g (34 mmol) of pyrrolidine and 0.6 g of copper(I) chloride in 150 ml of dry dioxane was stirred at 45° C. for 18 hours, then concentrated under reduced pressure, taken up in dichloromethane and extracted three times with 70 ml of 1 N hydrochloric acid each time, the acid extract was made alkaline with sodium carbonate, and the product was extracted by shaking with dichloromethane. Drying over sodium sulfate and evaporation under reduced pressure resulted in the Mannich base ($C_{22}H_{33}N_5O_3$; MW=415.55 g/mol) as oily crude product in virtually quantitative yield, which was converted into the fumarate with 3.5 g (30 mmol) of fumaric acid in analogy to Example 3F2).

Yield: 12.4 g (78% of theory); melting point: 151° C.
$C_{26}H_{37}N_5O_7$ (MW=531.62 g/mol)
Analysis Calculated: C 58.74% H 7.02% N 13.17%
Found: C 58.18% H 6.81% N 12.68%

EXAMPLE 5

1-(9-Diethylamino-6-hydroxy-6-methyl-7-nonynyl)-3-methyl-7-propylxanthine hydrochloride (by process variants D and F)

D1) 1-(6-Hydroxy-6-methyl-7-octynyl)-3-methyl-7-propylxanthine 16.2 ml (26 mmol) of 1.6 M n-butyllithium solution in n-hexane were added dropwise in 45 minutes to 2.55 g (26 mmol) of ethynyltrimethylsilane in 25 ml of tetrahydrofuran at −60° C. to −70° C. under a nitrogen atmosphere and with exclusion of moisture and stirring, the mixture was stirred at −70° C. for one hour and allowed to reach room temperature, and 6.4 g (20 mmol) of 3-methyl-1-(6-oxoheptyl)-7-propylxanthine in 20 ml of tetrahydrofuran were added dropwise in 20 minutes. The mixture was then stirred at room temperature for 4 hours, 50 ml of cold 1 N hydrochloric acid were added and, after exhaustive extraction with chloroform, the organic phase was dried over sodium sulfate and evaporated under reduced pressure, and the oily residue was purified by filtration through a silica gel column in the eluent chloroform/methanol (10:1), resulting in 6.8 g (81% of theory) of the alkynol trimethylsilylated on the ethynyl, $C_{21}H_{34}N_4O_3Si$ (MW=418.62 g/mol; melting point: 91° C.).

For desilylation, a solution of 4.19 g (10 mmol) of this product in 50 ml of methanol was, after addition of 58.1 mg (1 mmol) of potassium fluoride, stirred under reflux for 2 hours. It was then concentrated under reduced pressure, taken up in chloroform, washed with water and dried over sodium sulfate, and the solvent was removed under reduced pressure. The oily residue crystallized completely after lengthy standing and was extracted by stirring with petroleum ether.

Yield: 3.2 g (92% of theory); melting point: 79° C.
$C_{18}H_{26}N_4O_3$ (MW=346.44 g/mol)
Analysis: Calculated: C 62.41% H 7.56% N 16.17%
Found: C 62.23% H 7.41% N 16.41%

It was also possible to prepare this intermediate compound by reacting the oxoalkylxanthine with lithium acetylide both in analogy to Example 1D1) and in a reaction assisted by cerium(Ill) chloride as in Example 3D1), although the yields were distinctly lower at 30 to 50%, because in this specific case there was particularly noticeable interference from the tendency of the acetylene molecule to react at both ends with the ketone to form the alkynediol $C_{34}H_{50}N_8O_6$ (MW=666.84 g/mol; melting point: 129° C.) as byproduct, and isolation of the required monosubstituted product pure proved to involve very large losses.

D2) 1-(9-Diethylamino-6-hydroxy-6-methyl-7-nonynyl)-3-methyl-7-propylxanthine 10.4 g (30 mmol) of the intermediate compound prepared in stage D1) were subjected to the Mannich reaction in analogy to Example 4 using 2.49 g (34 mmol) of diethylamine in place of pyrrolidine. The oily crude product obtained was purified by filtration through a silica gel column in the eluent chloroform/methanol (10:1).

Yield: 8.3 g (64% of theory); oily product
$C_{23}H_{37}N_5O_3$ (MW=431.59 g/mol)

F3) 1-(9-Diethylamino-6-hydroxy-6-methyl-7-nonynyl)-3-methyl-7-propylxanthine hydrochloride The 8.3 g (19.2 mmol) of Mannich base from stage D2) were dissolved in methanol, and a stoichiometric amount of methanol in hydrochloric acid was added. The solvent was removed by distillation under reduced pressure, the residue was dried under high vacuum and digested with dry diethyl ether, and the solid was filtered off with suction.

Yield: 8.8 g (98% of theory); melting point: about 100° C. (hygroscopic); $C_{23}H_{38}ClN_5O_3$ (MW=468.05 g/mol)

EXAMPLE 6

1-(6-Dibutylamino-3-hydroxy-3-methyl-4-hexynyl)-3-methyl-7-propylxanthine hydrochloride (by process variants C and F)

C1) 1-(6-Dibutylamino-3-hydroxy-3-methyl-4-hexynyl)-3-methyl-7-propyl-xanthine 6.73 ml (10.77 mmol) of a 15% strength butyllithium solution in n-hexane were slowly added dropwise to a solution of 2.09 ml (10.77 mmol) of N,N-dibutyl-2-propynylamine in 20 ml of tetrahydrofuran at −65° C. The mixture was stirred at −60° C. to −65° C. for one hour and warmed to room temperature, and a solution of 2.0 g (7.18 mmol) of 3-methyl-1-(3-oxobutyl)-7-propylxanthine in 30 ml of tetrahydrofuran was added. The slightly exothermic reaction was complete after 30 minutes. The mixture was adjusted to pH 5–6 with 1 N hydrochloric acid and partitioned between dichloromethane and water. The organic phase was washed with water, dried with magnesium sulfate and concentrated under reduced pressure. The oily crude product was purified by flash chromatography, dichloromethane/methanol =19/0.75.

Yield: 2.37 g (74% of theory); melting point: 73° C.
$C_{24}H_{39}N_5O_3$ (MW=445.61 g/mol)

F2) 1-(6-Dibutylamino-3-hydroxy-3-methyl-4-hexynyl)-3-methyl-7-propylxanthine hydrochloride 597 mg (1.34 mmol) of the xanthine prepared in stage C1) were dissolved in 1.34 ml of 1 N hydrochloric acid, concentrated under high vacuum, extracted by stirring with diethyl ether for 2 days and filtered.

Yield: 591 mg (91% of theory); melting point: 179° C.
$C_{24}H_{40}ClN_5O_3$ (MW=482.07 g/mol)
Mass spectrum: 446.5 (100%, M+H); 428.5 (32%)

EXAMPLE 7

1-(6-N-Benzyl-N-methylamino-3-hydroxy-3-methyl-4-hexynyl)-3-methyl-7-propylxanthine fumarate (by process variants C and F)

C1) 1-(6-N-Benzyl-N-methylamino-3-hydroxy-3-methyl-4-hexynyl)-3-methyl-7-propylxanthine 1-(6-N-Benzyl-N-methylamino-3-hydroxy-3-methyl-4-hexynyl)-3-methyl-7-propylxanthine was prepared as oily substance in 86% yield using 3-methyl-1-(3-oxobutyl)-7-propylxanthine and N-benzyl-N-methyl-2-propynylamine as in Example 6C1). $C_{24}H_{31}N_5O_3$ (MW=437.55 g/mol)

F2) 1-(6-N-Benzyl-N-methylamino-3-hydroxy-3-methyl-4-hexynyl)-3-methyl-7-propylxanthine fumarate 540 mg (1.23 mmol) of the xanthine prepared in stage C1) were dissolved in ethanol, a hot solution of 146 mg (1.23 mmol) of fumaric acid in ethanol was added, and the mixture was stirred at 50° C. for 30 minutes. It was concentrated under high vacuum, extracted by stirring with diethyl ether and filtered.

Yield: 570 mg (83% of theory); melting point: 104° C.
$C_{28}H_{35}N_5O_7$ (MW=553.62 g/mol)
Mass spectrum: 438.4 (100%, M+H); 420.4 (87%)

EXAMPLE 8

1-(4-Hydroxy-4-methyl-7-[4-methylpiperazino]-5-heptynyl)-3-methyl-7-propylxanthine fumarate
by process variants C and F:

C1) 4-Methyl-1-(2-propynyl)-piperazine 11.1 ml (0.10 mol) of an 80% strength 2-propynyl bromide solution in toluene were added to a solution of 22.2 ml (0.20 mol) of N-methyl-piperazine in 100 ml of toluene while cooling in ice. After 30 minutes under reflux, the resulting N-methylpiperazine hydrobromide was filtered off with suction and washed with toluene, and the filtrate was washed twice each with 15% strength sodium hydroxide solution and saturated sodium chloride solution, concentrated and distilled in vacuo.

Yield: 4.19 g (30% of theory); boiling point: 100° C./47 mbar (GC: 98.6%)
$C_8H_{14}N_2$ (MW=138.21 g/mol)
Mass spectrum: 139.2 (100%, M+H); 138.2 (22%); 101.1 (24%); $^1$H-NMR (DMSO-$d_6$, 300 MHz): δ=2.10–2.54 (m, 8 H, $CH_2$); 2.13 (s, 3 H, $NCH_3$); 3.12 (t, 1 H, C≡CH; 3.23 (d, 2 H, $NCH_2$C≡C)

C2) 1-(4-Hydroxy-4-methyl-7-[4-methylpiperazino]-5-heptynyl)-3-methyl-7-propylxanthine fumarate 1-(4-Hydroxy-4-methyl-7-[4-methylpiperazino]-5-heptynyl)-3-methyl-7-propylxanthine was prepared as oily substance in 82% yield using 3-methyl-1-(4-oxopentyl)-7-propylxanthine and 4-methyl-1-(2-propynyl)-piperazine from stage C1) as in Example 6C1). Salt formation with fumaric acid took place as in Example 7F2) in 55% yield.

Melting point: 168° C.
$C_{26}H_{38}N_6O_7$ (MW=546.63 g/mol), base $C_{22}H_{34}N_6O_3$ (MW=430.56 g/mol)
Mass spectrum: 431.4 (100%, M+H); 413.4 (7%)
by process variant D:

D1) 1-(4-Hydroxy-4-methyl-5-hexynyl)-3-methyl-7-propylxanthine

This intermediate compound of the formula IX was synthesized from 3-methyl-1-(4-oxopentyl)-7-propylxanthine both by ethynylation with lithium acetylide assisted by cerium(III) chloride as in Example 3D1) in 67% yield and by reaction with lithiated ethynyltrimethylsilane and subsequent desilylation in analogy to Example 5D1) in a total yield of 69%.

$C_{16}H_{22}N_4O_3$ (MW=318.38 g/mol); melting point: 108° C.
Analysis: Calculated: C 60.36% H 6.97% N 17.60%
Found: C 60.09% H 7.10% N 17.39%

Mannich reaction of this product with N-methylpiperazine and paraformaldehyde under the reaction conditions described in Example 4 likewise resulted in the title compound of the present example in the form of the base.

EXAMPLE 9

1-(5-Diethylamino-2-hydroxy-2-methyl-3-pentynyl)-3-methyl-7-propylxanthine fumarate (by process variants C and F)

1-(5-Diethylamino-2-hydroxy-2-methyl-3-pentynyl)-3-methyl-7-propylxanthine was prepared as oily substance in 48% yield using 3-methyl-1-(2-oxopropyl)-7-propylxanthine and N,N-diethyl-2-propynylamine as in Example 6C1). Salt formation with fumaric acid as in Example 7F2) took place in 98% yield. Melting point: 109° C. $C_{23}H_{33}N_5O_7$ (MW=491.56 g/mol), base $C_{19}H_{29}N_5O_3$ (MW=375.48 g/mol)

Mass spectrum: 376.2 (30%, M+H); 358.2 (66%); 285.1 (100%); 150.2 (48%)

EXAMPLE 10

1-(7-Dipropylamino-4-hydroxy-4-methyl-5-heptynyl)-3-ethyl-7-propylxanthine hemifumarate (by process variants C and F)

C1) 1-(7-Dipropylamino-4-hydroxy-4-methyl-5-heptynyl)-3-ethyl-7-propyl-xanthine 5.3 ml (8.45 mmol) of a 15% strength butyllithium solution in n-hexane were slowly added dropwise to a solution of 1.36 ml (7.8 mmol) of N,N-dipropyl-2-propynylamine in 6 ml of tetrahydrofuran at −78° C., and the mixture was stirred at −78° C. for one hour. After warming to room temperature, a solution of 2.0 g (6.5 mmol) of 3-ethyl-1-(4-oxopentyl)-7-propylxanthine in 8 ml of tetrahydrofuran was added. After 7 hours at room temperature, the mixture was adjusted to pH 6–7 with 4 N hydrochloric acid and partitioned between 5% strength sodium bicarbonate solution and dichloromethane. The organic phase was dried with magnesium sulfate, concentrated under reduced pressure and purified by flash chromatography, dichloromethane/methanol=19/1.

Yield: 0.71 g (24% of theory), oily product
$C_{24}H_{39}N_5O_3$ (MW=445.62 g/mol)

F2) 1-(7-Dipropylamino-4-hydroxy-4-methyl-5-heptynyl)-3-ethyl-7-propyl-xanthine hemifumarate Salt formation to give the hemifumarate took place with 1 equivalent of fumaric acid as in Example 7F2) in 86% yield. Melting point: 117° C.

$C_{26}H_{41}N_5O_5$ (MW=503.65 g/mol)

Mass spectrum: 446.2 (100%, M+H); 329.2 (50%); 307.1 (56%); 100.1 (83%); $^1$H-NMR (DMSO-$d_6$, 200 MHz): δ=0.79 (t, 6 H, N((CH$_2$)$_2$CH$_3$)$_2$); 0.83 (t, 3 H, N$^7$(CH$_2$)$_2$-CH$_3$); 1.23 (t, 3 H, N$^3$CH$_2$CH$_3$); 1.33 (s, 3 H, CH$_3$); 1.26–1.89 (m, 10 H, CH$_2$); 2.32 (t, 4 H, N(CH$_2$CH$_2$CH$_3$)$_2$); 3.31 (s, 2 H, NCH$_2$C≡C); 3.88 (t, 2 H, N$^1$-CH$_2$); 4.03 (q, 2 H, N$^3$-CH$_2$); 4.20 (t, 2 H, N$^7$-CH$_2$); 5.12 (s, 1 H, OH); 6.61 (s, 1 H, C=CH-COOH); 8.10 (s, 1 H, N=CH)

EXAMPLE 11

1-(8-Dimethylamino-5-hydroxy-5-methyl-6-octynyl)-3-ethyl-7-propylxanthine fumarate (by process variants C and F)

1-(8-Dimethylamino-5-hydroxy-5-methyl-6-octynyl)-3-ethyl-7-propylxanthine was prepared as oily substance in 57% yield using 3-ethyl-1-(5-oxohexyl)-7-propylxanthine and N,N-dimethyl-2-propynylamine as in Example 6C1). Salt formation to give the fumarate took place as in Example 7F2) in 51% yield. Melting point: 117° C.

$C_{25}H_{37}N_5O_7$ (MW=519.60 g/mol), base $C_{21}H_{33}N_5O_3$ (MW=403.54 g/mol)

Mass spectrum: 404.2 (100%, M+H); 386.2 (44%); 321.2 (49%)

EXAMPLE 12

3-Ethyl-1-(3-hydroxy-3-methyl-6-pyrrolidino-4-hexynyl)-7-propylxanthine fumarate (by process variants C and F)

3-Ethyl-1-(3-hydroxy-3-methyl-6-pyrrolidino-4-hexynyl)-7-propylxanthine as prepared as oily substance in 50% yield using 3-ethyl-1-(3-oxobutyl)-7-propylxanthine and N-(2-propynyl)pyrrolidine as in Example 6C1). Salt formation to give the fumarate took place as in Example 7F2) in 90% yield. Melting point: 133° C.

$C_{25}H_{35}N_5O_7$ (MW=517.59 g/mol), base $C_{21}H_{31}N_5O_3$ (MW=401.52 g/mol)

Mass spectrum: 402.2 (100%, M+H); 116.9 (65%)

EXAMPLE 13

3,7-Dipropyl-1-(5-hydroxy-5-methyl-8-[4-methylpiperazino]-6-octynyl)xanthine fumarate (by process variants C and F)

3,7-Dipropyl-1-(5-hydroxy-5-methyl-8-[4-methylpiperazino]-6-octynyl)-xanthine was prepared as oily substance in 71% yield using 3,7-dipropyl-1-(5-oxohexyl)xanthine and 4-methyl-1-(2-propynyl)piperazine from Example 8C1) as in Example 6C1). Salt formation to give the fumarate took place as in Example 7F2) in 95% yield. Melting point: 98° C.

$C_{29}H_{44}N_6O_7$ (MW=588.71 g/mol), base $C_{25}H_{40}N_6O_3$ (MW=472.64 g/mol)

Mass spectrum: 473.2 (98%, M+H); 335.1 (95%); 138.9 (100%); 85.1 (67%)

EXAMPLE 14

3-Butyl-1-(5-hydroxy-5-methyl-8-piperidino-6-octynyl)-7-propylxanthine hydrochloride (by process variants C and F)

C1) 3-Butyl-1-(5-hydroxy-5-methyl-8-piperidino-6-octynyl)-7-propylxanthine

The compound was prepared as oily substance in 58% yield using 3-butyl-1-(5-oxohexyl)-7-propylxanthine and N-(2-propynyl)piperidine as in Example 6C1).

$C_{26}H_{41}N_5O_3$ (MW=471.65 g/mol)

F2) 3-Butyl-1-(5-hydroxy-5-methyl-8-piperidino-6-octynyl)-7-propylxanthine hydrochloride 470 mg (1 mmol) of the xanthine prepared in stage C1) were dissolved in methanol, 1 ml of 1 N hydrochloric acid was added, and the mixture was concentrated under high vacuum, extracted by stirring with acetone and filtered.

Yield: 450 mg (84% of theory), melting point: 177° C.
$C_{26}H_{42}ClN_5O_3$ (MW=508.11 g/mol)

Mass spectrum: 472.5 (100%, M+H); 454.4 (12%)

EXAMPLE 15

3-Butyl-1-(6-dipropylamino-3-hydroxy-3-methyl-4-hexynyl)-7-propylxanthine (by process variant C)

3-Butyl-1-(6-dipropylamino-3-hydroxy-3-methyl-4-hexynyl)-7-propylxanthine was prepared in 28% yield using 3-butyl-1-(3-oxobutyl)-7-propylxanthine and N,N-dipropyl-2-propynylamine as as in Example 6C1).

Melting point: 101° C.; $C_{25}H_{41}N_5O_3$ (MW=459.64 g/mol)

Mass spectrum: 460.2 (100%; M+H); 442.2 (15%)

EXAMPLE 16

3-Butyl-1-(5-hydroxy-5-methyl-8-morpholino-6-octynyl)-7-propylxanthine hydrochloride (by process variants C und F)

3-Butyl-1-(5-hydroxy-5-methyl-8-morpholino-6-octynyl)-7-propylxanthine was prepared as oily substance in 76% yield using 3-butyl-1-(5-oxohexyl)-7-propylxanthine and N-(2-propynyl)morpholine as in Example 6C1). Salt formation to give the hydrochloride took place as in Example 14F2) in 86% yield. Melting point: 126° C.

$C_{25}H_{40}ClN_5O_4$ (MW=510.08 g/mol), base $C_{25}H_{39}N_5O_4$ (MW=473.63 g/mol)

Mass spectrum: 474.3 (100%, M+H); 456.4 (83%)

EXAMPLE 17

7-(8-Diethylamino-5-hydroxy-5-methyl-6-octynyl)-3-methyl-1-propylxanthine hydrochloride by process variants C and F:

7-(8-Diethylamino-5-hydroxy-5-methyl-6-octynyl)-3-methyl-1-propylxanthine was prepared as oily substance in 35% yield using 3-methyl-7-(5-oxohexyl)-1-propylxanthine and N,N-diethyl-2-propynylamine as in Example 6C1). Salt formation to give the hydrochloride took place as in Example 14F2) in 64% yield. Melting point: 127° C.

$C_{22}H_{36}ClN_5O_3$ (MW=454.01 g/mol), base $C_{22}H_{35}N_5O_3$ (MW=417.55 g/mol)

Mass spectrum: 418.3 (100%, M+H); 400.3 (35%)

by process variants B and F:

B1) 7-(5-Hydroxy-5-methyl-6-heptynyl)-3-methylxanthine 33.2 g (0.2 mol) of 3-methylxanthine in 350 ml of dimethylformamide were stirred with 32.1 g (0.2 mol) of 1-chloro-5-hydroxy-5-methyl-6-heptyne from Example 1B1) in the presence of 13.8 g (0.1 mol) of potassium carbonate at 120° C. for 6 hours. The hot mixture was then filtered, evaporated to dryness under reduced pressure and taken up in ethanol and, at the boiling point, diisopropyl ether was added to cloudiness, and the mixture was left to crystallize with cooling.

Yield: 38.8 g (67% of theory); melting point: 173° C.

$C_{14}H_{18}N_4O_3$ (MW=290.33 g/mol)

Analysis: Calculated: C 57.92% H 6.25% N 19.30%

Found: C 57.62% H 6.27% N 19.20%

B2) 7-(5-Hydroxy-5-methyl-6-heptynyl)-3-methyl-1-propylxanthine 19.5 g (67 mmol) of the intermediate compound from stage B1), 9.3 g (67 mmol) of potassium carbonate and 8.24 g (67 mmol) of propyl bromide were reacted in 200 ml of dimethylformamide as described in stage B1). The oily crude product was purified by filtration through a silica gel column with ethyl acetate as eluent and subsequent crystallization of the solid from diisopropyl ether with the addition of ethyl acetate at the boiling point until the solution was clear.

Yield: 15.1 g (68% of theory); melting point: 97° C.

$C_{17}H_{24}N_4O_3$ (MW=332.41 g/mol)

Analysis: Calculated: C 61.42% H 7.28% N 16.86%

Found: C 61.20% H 7.39% N 16.74%

The products of stages B1) and B2) are, as compounds of the formula IX, amenable to the Mannich reaction. Thus, reaction of the alkynol from stage B2) with diethylamine and paraformaldehyde in analogy to Example 4 and salt formation as in Example 1F3) likewise afforded the title compound of the present example.

EXAMPLE 18

1,7-Bis-(8-diethylamino-5-hydroxy-5-methyl-6-octynyl)-3-methylxanthine (by process variant C)

The compound was prepared as oily substance in 30% yield using 1,7-bis-(5-oxohexyl)-3-methylxanthine and N,N-diethyl-2-propynylamine as in Example 6C1).

$C_{32}H_{52}N_6O_4$ (MW=584.82 g/mol) $^1$H-NMR (DMSO-$d_6$, 300 MHz): δ=0.93 and 0.94 (2 t, 12 H, N(CH$_2$CH$_3$)$_2$); 1.20–1.62 and 1.71–1.85 (m, 12 H, CH$_2$); 1.31 (s, 6 H, CH$_3$); 2.32–2.48 (m, 8 H, N(CH$_2$CH$_3$)$_2$); 3.35 (2 s, 4 H, NCH$_2$C≡C); 3.42 (s, 3 H, N$^3$CH$_3$); 3.80–3.90 (m, 2 H, N$^7$CH$_2$); 4.24 (t, 2 H, N$^1$CH$_2$); 5.10 and 5.11 (2 s, 2 H, OH); 8.08 (s, 1 H, N=CH)

EXAMPLE 19

1-(7-Dipropylamino-4-hydroxy-4-methyl-5-heptynyl)-3-methylxanthine by process variant C:

The compound was prepared as oily substance in 51% yield as in Example 6C1) from 3-methyl-1-(4-oxopentyl)xanthine and N, N-dipropyl-2-propynylamine.

$C_{20}H_{31}N_5O_3$ (MW=389.51 g/mol)

Mass spectrum: 390.2 (100%, M+H); 372.2 (47%)

$^1$H-NMR (DMSO-$d_6$, 300 MHz): δ=0.80 (t, 6 H, N(CH$_2$)$_2$-CH$_3$); 1.32–1.88 (m, 8 H, CH$_2$); 1.32 (s, 3 H, C(OH)CH$_3$); 2,32 (m br., 4 H, NCH$_2$-C$_2$H$_5$); 3.33 (s, 2 H, NCH$_2$-C≡C); 3.45 (s, 3 H, N$^3$-CH$_3$); 3.90 (t, 2 H, N$^1$-CH$_2$); 5.12 (s, 1 H, OH; 8.04 (s, 1 H, N=CH); 13.53 (s br., 1 H, N$^7$-H)

by process variant B:

B1) 7-Ethoxymethyl-1-(5-hydroxy-5-methyl-6-heptynyl)-3-methylxanthine 44.84 g (0.2 mol) of 7-ethoxymethyl-3-methylxanthine were reacted with 32.13 g (0.2 mol) of 1-chloro-5-hydroxy-5-methyl-6-heptyne from Example 1B1), and worked up in analogy to Example 1B2).

Yield: 52.3 g (75% of theory); melting point: 106° C.

$C_{17}H_{24}N_4O_4$ (MW=348.41 g/mol)

Analysis: Calculated: C 58.61% H 6.94% N 16.08%

Found: C 58.41% H 7.08% N 15.97%

B2) 1-(5-Hydroxy-5-methyl-6-heptynyl)-3-methylxanthine 41.8 g (0.12 mol) of the alkynol from stage B1) were stirred in 600 ml each of 1 N hydrochloric acid and glacial acetic acid at 60° C. for 4 hours. The mixture was then concentrated under reduced pressure and neutralized with 1 N sodium hydroxide solution, the product was extracted with chloroform, the extract was dried over sodium sulfate and evaporated under reduced pressure, and the residue was subjected to purification by flash chromatography with chloroform as mobile phase and then recrystallization from ethanol/petroleum ether.

Yield: 23.6 g (68% of theory); melting point: 172° C.

$C_{14}H_{18}N_4O_3$ (MW=290.33 g/mol)

Analysis: Calculated: C 57.92% H 6.25% N 19.30%

Found: C 57.65% H 6.25% N 19.33%

Mannich reaction of this intermediate compound with dipropylamine and paraformaldehyde as in Example 4 likewise resulted in the title compound of the present example.

EXAMPLE 20

3-Cyclopropyl-1-(8-diethylamino-5-hydroxy-5-methyl-6-octynyl)-7-propylxanthine hydrochloride (by process variants C and F)

3-Cyclopropyl-1-(8-diethylamino-5-hydroxy-5-methyl-6-octynyl)-7-propylxanthine was prepared as oily substance in 89% yield as in Example 6C1) from 3-cyclopropyl-1-(5-oxohexyl)-7-propylxanthine and N,N-diethyl-2-propynylamine. Salt formation to give the hydrochloride took place as in Example 6F2) in 93% yield. Melting point: 146° C.

$C_{24}H_{38}ClN_5O_3$ (MW=480.06 g/mol), base: $C_{24}H_{37}N_5O_3$ (MW=443.60 g/mol)

Mass spectrum: 444.3 (100%; M+H); 426.3 (41%); 253.1 (21%)

EXAMPLE 21

1-(8-Diethylamino-5-hydroxy-6-octynyl)-3-methyl-7-propylxanthine hydrochloride (by process variants C and F)

C1) 1-(8-Diethylamino-5-hydroxy-6-octynyl)-3-methyl-7-propylxanthine 2.93 ml (4.68 mmol) of a 15% strength butyllithium solution in n-hexane were slowly added dropwise to a stirred solution of 676 μl (4.9 mmol) of N,N-diethyl-2-propynylamine in 4 ml of tetrahydrofuran at −78° C. under argon. The mixture was stirred at this temperature for one hour and, after warming to room temperature, a solution of 1.05 g (3.6 mmol) of 3-methyl-1-(5-oxopentyl)-7-propylxanthine in 5 ml of tetrahydrofuran was slowly added. The reaction was complete after 1.5 hours.

Neutralization was carried out with 4 N hydrochloric acid, the tetrahydrofuran was stripped off in vacuo, the residue was taken up in dichloromethane, the solution was washed with saturated sodium bicarbonate solution and dried over magnesium sulfate, the desiccant was filtered off, and the solvent was removed under reduced pressure. The crude product was purified by flash chromatography with a dichloromethane/methanol/saturated ammonia solution=19/1/0.05 mixture as mobile phase.

Yield: 1.1 g (76% of theory); yellowish oil $C_{21}H_{33}N_5O_3$ (MW=403.53 g/mol)

F2) 1-(8-Diethylamino-5-hydroxy-6-octynyl)-3-methyl-7-propylxanthine hydrochloride 430 mg (1.07 mmol) of the xanthine prepared in stage C1) were dissolved in 1.07 ml of 1 N hydrochloric acid and, after concentration under high vacuum, pentane was added and the mixture was stirred for 3 days. After the pentane had been stripped off, diethyl ether was added, and the mixture was stirred for a further four weeks until crystallization was complete. The ether was stripped off and the residue was again stirred with pentane for 10 minutes. After the pentane had been stripped off, the residue was again treated with pentane, which was subsequently removed completely in a rotary evaporator and then under high vacuum. The product remained as a white solid.

Yield: 460 mg (98% of theory); melting point: 65° C.

$C_{21}H_{34}ClN_5O_3$ (MW=439.99 g/mol)

Mass spectrum: 404.3 (100%, M+H)

EXAMPLE 22

1-(8-Amino-5-hydroxy-5-methyl-6-octynyl)-3-methyl-7-propylxanthine hydrochloride (by process variants C and F)

C1) N,N'-Bis-(trimethylsilyl)-2-propynylamine 32 ml (154 mmol) of hexamethyldisilazane were slowly added dropwise to a stirred solution of 95 ml of ether and 95 ml (152 mmol) of a 15% strength butyllithium solution in n-hexane at −78° C. under argon. The mixture was allowed to reach room temperature, was stirred for one hour and cooled to −20° C., and 8.24 ml (73 mmol) of an 80% strength solution of 2-propynyl bromide in toluene were then slowly added dropwise. After the addition, the cooling bath was removed and the mixture was stirred at room temperature for 5 hours. The reaction mixture was subsequently added to 200 ml of phosphate buffer composed of 7.36 g of potassium dihydrogen phosphate, 5.81 g of disodium hydrogen phosphate and 200 ml of water. The precipitate was filtered off with suction, the phases were separated, the organic phase was washed with water and dried over sodium carbonate, the desiccant was filtered off, the solvent was removed in a rotary evaporator, and the residue was fractionated twice by vacuum distillation.

Yield: 9.26 g (63% of theory); boiling point: 50° C./4 mbar $C_9H_{21}NSi_2$ (MW=199.45 g/mol)

$^1$H-NMR (DMSO-$d_6$, 250 MHz): δ=0.11 (s, 18 H, C[Si(CH$_3$)$_3$]$_2$); 3.00 (t, 1 H, C≡CH; 3.50 (d, 2 H, NCH$_2$C≡C)

C2) 1-(8-Amino-5-hydroxy-5-methyl-6-octynyl)-3-methyl-7-propylxanthine 29 ml (46.5 mmol) of a 15% strength butyllithium solution in n-hexane were slowly added dropwise to a stirred solution of 9.26 g (46.5 mmol) of N,N-bis(trimethylsilyl)-2-propynylamine from stage C1 in 50 ml of tetrahydrofuran at −40° C. under argon. The mixture was then warmed to room temperature and again cooled to −40° C., and a solution of 14.25 g (46.5 mmol) of 3-methyl-1-(5-oxohexyl)-7-propylxanthine in 40 ml of tetrahydrofuran was slowly added. After removal of the cooling bath, the mixture was stirred at room temperature for 6 hours. The reaction mixture was then added to saturated ammonium chloride solution at 0° C., the aqueous phase was extracted with ether, the organic phase was dried over sodium sulfate, the desiccant was filtered off, and the solvent was removed under reduced pressure. The crude product was subjected to flash chromatography first with the mobile phase mixture dichloromethane/methanol/saturated ammonia solution=19/1.5/2.5 and then with 9/1/2.5. Yield: 9.79 g (58% of theory); yellowish oil $C_{18}H_{27}N_5O_3$ (MW=361.45 g/mol)

The compound can likewise be obtained by direct reaction with 2-propynylamine: 5.3 ml (8.49 mmol) of a 15% strength butyllithium solution in n-hexane were slowly added dropwise to a stirred solution of 630 μl (9.1 mmol) of 2-propynylamine in 20 ml of tetrahydrofuran at −78° C. under argon. The mixture was stirred at this temperature for one hour and warmed to room temperature, and a solution of 2.0 g (6.53 mmol) of 3-methyl-1-(5-oxohexyl)-7-propylxanthine in 5 ml of tetrahydrofuran was slowly added to the suspension which had become yellow. The reaction had ceased after 3 hours. The mixture was neutralized with 2 N hydrochloric acid and 5% strength sodium bicarbonate solution and extracted with dichloromethane and, after drying over magnesium sulfate, the desiccant was filtered off and the solvent was removed under reduced pressure. The crude product was purified by flash chromatography with the mobile phase mixture dichloromethane/methanol/saturated ammonia solution=19/1/0.02. Since the 1.4 g of product which were obtained were still slightly impure, they were subjected to renewed flash chromatography (mobile phase mixture dichloromethane/methanol/saturated ammonia solution=9/1.5/0.02).

Yield: 1.01g (43%); yellowish oil

F3) 1-(8-Amino-5-hydroxy-5-methyl-6-octynyl)-3-methyl-7-propylxanthine hydrochloride 940 mg (2.6 mmol) of the xanthine prepared in stage C2) were dissolved in 2.6 ml of 1 N hydrochloric acid and, after concentration under high vacuum, pentane was added and the mixture was stirred for 3 weeks. The resulting solid was filtered off with suction. The portion which had already liquefied again (hygroscopic) was returned to a flask, dissolved in a little water, dried in vacuo and, after renewed addition of pentane, stirred. After two days, the pentane was stripped off and the remaining powdery solid was separated from the uncrystallized product.

Yield: 587 mg (57% of theory) of white solid; melting point: 80° C. 345 mg (33% of theory) of uncrystallized product $C_{18}H_{28}ClN_5O_3$ (MW=397.91 g/mol), base: $C_{18}H_{27}N_5O_3$ (MW=361.45 g/mol)

Mass spectrum: 362.3 (7%, M+H); 344.2 (59%); 209.0 (100%)

EXAMPLE 23

1-(8-Ethylamino-5-hydroxy-5-methyl-6-octynyl)-3-methyl-7-propylxanthine (by process variant C)

C1) N-Ethyl-2-propynylamine 33 ml (0.5 mol) of ethylamine were condensed at −78° C. in a flask which had been bleached and flushed with argon. After warming to 0° C., 5.57 ml (50 mmol) of an 80% strength solution of 2-propynyl bromide in toluene were slowly added dropwise over the course of 45 minutes. A gas chromatogram after one hour showed that the reaction was complete. The excess of ethylamine was driven out with nitrogen after removal of the ice bath, the residue was taken up in a mixture of ether and water, the aqueous phase was extracted several times with ether, the combined ether phases were dried with potassium carbonate, the desiccant was filtered off and the filtrate was concentrated in a rotary evaporator. Subsequent fractional distillation afforded 937 mg (18% of theory) of a mixture of 83% N-ethyl-2-propynylamine and 17% toluene, which was immediately reacted further. $C_5H_9N$ (MW=83.15 g/mol)

$^1$H-NMR (CDCl$_3$, 250 MHz): δ=1.12 (t, 3 H, CH$_2$CH$_3$); 1.30 (s br, NH); 2.20 (t, 1 H, C≡CH); 2.74 (q, 2 H, CH$_2$CH$_3$); 3.42 (d, 2 H, NCH$_2$C≡C)

C2) 1-(8-Ethylamino-5-hydroxy-5-methyl-6-octynyl)-3-methyl-7-propylxanthine 5.43 ml (8.69 mmol) of a 15% strength butyllithium solution in n-hexane were slowly added dropwise to a stirred solution of 937 mg (9.35 mmol) of N-ethyl-2-propynylamine (83% strength in toluene from stage C1) in 30 ml of tetrahydrofuran at −78° C. under argon. The mixture was stirred at this temperature for one hour and warmed to room temperature, and a solution of 2.05 g (6.68 mmol) of 3-methyl-1-(5-oxohexyl)-7-propylxanthine in 12 ml of tetrahydrofuran was slowly added to the suspension which was now white. After one hour, the mixture was neutralized with 2 N hydrochloric acid and 5% strength sodium bicarbonate solution and extracted with dichloromethane and, after drying over magnesium sulfate, the desiccant was filtered off and the solvent was removed under reduced pressure. The crude product was purified by flash chromatography with the mobile phase mixture dichloromethane/methanol/saturated ammonia solution=19/1.5/0.02.

Yield: 2.35 g (90%); oil 1.3 g of the product still contaminated with dichloromethane were dissolved in a mixture of acetone and water and subsequently the solvents were removed again in a rotary evaporator and then under high vacuum. 1.3 g of a viscous, solvent-free oil remained.

$C_{20}H_{31}N_5O_3$ (MW=389.56 g/mol)

Mass spectrum: 390.2 (100%, M+H); 372.2 (28%); 209.1 (47%);

$^1$H-NMR (DMSO-d$_6$, 200 MHz): δ=0.85 (t, 3 H, N$^7$(CH$_2$)$_2$CH$_3$); 0.98 (t, 3 H, NCH$_2$CH$_3$); 1.30–1.65 (m, 6 H, CH$_2$); 1.30 (s, 3 H, C(OH)CH$_3$); 1.79 (sex, 2 H, N$^7$CH$_2$CH$_2$CH$_3$); 2.56 (q, 2 H, NCH$_2$CH$_3$); 3.30 (s, 2 H, NCH$_2$C≡C); 3.44 (s, 3 H, N$^3$CH$_3$); 3.77–3.95 (m, 2 H, N$^1$CH$_2$); 4.21 (t, 2 H, N$^7$CH$_2$); 5.07 (s, 1 H, OH); 8.10 (s, 1 H, N=CH

EXAMPLE 24

1-(8-Ethylpropylamino-5-hydroxy-5-methyl-6-octynyl)-3-methyl-7-propylxanthine (by process variant E)

650 mg (1.67 mmol) of 1-(8-ethylamino-5-hydroxy-5-methyl-6-octynyl)-3-methyl-7-propylxanthine from Example 23 were dissolved in 30 ml of ethanol. After cooling to −78° C., 602 μl (8.34 mmol) of propionaldehyde were added and, after warming to 0° C., 105 mg (1.67 mmol) of sodium cyanoborohydride were added. In order to complete the reaction, a spatula tip of sodium cyanoborohydride was added after 2 hours, and a further 602 μl (8.34 mmol) of propionaldehyde and 105 mg (1.67 mmol) of sodium cyanoborohydride were added after 3 hours. After the reaction was complete, the reaction mixture was concentrated in a rotary evaporator under reduced pressure, sodium bicarbonate solution was added to the residue, the aqueous phase was extracted with dichloromethane, the combined extracts were dried with magnesium sulfate, the desiccant was filtered off, and the filtrate was concentrated under reduced pressure in a rotary evaporator. The crude product was purified by flash chromatography with the mobile phase mixture dichloromethane/methane/saturated ammonia solution=19/1/0.02.

Yield: 503 mg (70%); oil $C_{23}H_{37}N_5O_3$ (MW=431.65 g/mol); mass spectrum: 432.4 (100%, M+H); 414.3 (44%);

$^1$H-NMR (DMSO-d$_6$, 200 MHz): δ=0.75–0.88 (2 t, 6 H, N(CH$_2$)$_2$CH$_3$, N$^7$(CH$_2$)$_2$CH$_3$); 0.94 (t, 3 H, NCH$_2$CH$_3$); 1.30–1.68 (m, 8 H, CH$_2$); 1.30 (s, 3 H, C(OH)CH$_3$); 1.79 (sex, 2 H, N$^7$CH$_2$-CH$_2$CH$_3$); 2.24–2.45 (m, 4 H, NCH$_2$CH$_2$CH$_3$, NCH$_2$CH$_3$); 3.32 (s, 2 H, NCH$_2$C≡C); 3.43 (s, 3 H, N$^3$CH$_3$); 3.76–3.95 (m, 2 H, N$^1$CH$_2$); 4.21 (t, 2 H, N$^7$CH$_2$); 5.06 (s, 1 H, OH; 8.10 (s, 1 H, N=CH)

TABLE 1

Compounds of the formula I

[Structure: xanthine core with R1 on N, R2 on N, R3 on N]

| Ex. | R¹ | R² | R³ | isolated as | M.p.[°C] |
|---|---|---|---|---|---|
| 1 | [diethylamino-CH2-C≡C-C(CH3)(OH)-(CH2)4-] | —CH₃ | —(CH₂)₂—CH₃ | Hydrochloride | 132 |
| 1a | [diethylamino-CH2-C≡C-C(CH3)(OH)-(CH2)4-] (+)-Enantiomer | —CH₃ | —(CH₂)₂—CH₃ | Hydrochloride | 86 |
| 1b | [diethylamino-CH2-C≡C-C(CH3)(OH)-(CH2)4-] (−)-Enantiomer | —CH₃ | —(CH₂)₂—CH₃ | Hydrochloride | 89 |
| 2 | [triethylammonium-CH2-C≡C-C(CH3)(OH)-(CH2)4-] | —CH₃ | —(CH₂)₂—CH₃ | Iodide | 160 |
| 3 | [dimethylamino-CH2-C≡C-C(CH3)(OH)-(CH2)2-] | —CH₃ | —(CH₂)₂—CH₃ | Fumarate | 170 |

TABLE 1-continued
Compounds of the formula I
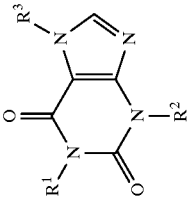
| Ex. | R¹ | R² | R³ | isolated as | M.p.[°C.] |
|---|---|---|---|---|---|
| 4 |  | —CH₃ | —(CH₂)₂—CH₃ | Fumarate | 151 |
| 5 |  | —CH₃ | —(CH₂)₂—CH₃ | Hydrochloride | >>100 |
| 6 | 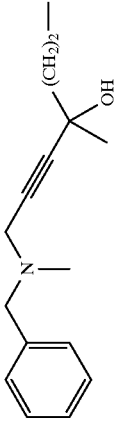 | —CH₃ | —(CH₂)₂—CH₃ | Hydrochloride | 179 |
| 7 | 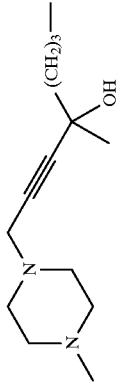 | —CH₃ | —(CH₂)₂—CH₃ | Fumarate | 104 |
| 8 |  | —CH₃ | —(CH₂)₂—CH₃ | Fumarate | 168 |

TABLE 1-continued
Compounds of the formula I
| Ex. | R¹ | R² | R³ | isolated as | M.p.[°C.] |
|---|---|---|---|---|---|
| 9 | 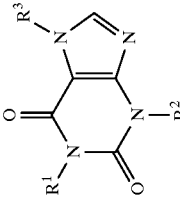 | —CH₃ | —(CH₂)₂—CH₃ | Fumarate | 109 |
| 10 |  | —C₂H₅ | —(CH₂)₂—CH₃ | Hemifumarate | 117 |
| 11 |  | —C₂H₅ | —(CH₂)₂—CH₃ | Fumarate | 117 |
| 12 |  | —C₂H₅ | —(CH₂)₂—CH₃ | Fumarate | 133 |
| 13 |  | —(CH₂)₂—CH₃ | —(CH₂)₂—CH₃ | Fumarate | 98 |

TABLE 1-continued

Compounds of the formula I

| Ex. | R¹ | R² | R³ | isolated as | M.p.[°C.] |
|---|---|---|---|---|---|
| 14 | piperidinyl-CH₂-C≡C-C(CH₃)(OH)-(CH₂)₄- | —(CH₂)₃—CH₃ | —(CH₂)₂—CH₃ | Hydrochloride | 177 |
| 15 | CH₃(C₃H₇)N-CH₂-C≡C-C(CH₃)(OH)-(CH₂)₃- | —(CH₂)₃—CH₃ | —(CH₂)₂—CH₃ | Base | 101 |
| 16 | morpholinyl-CH₂-C≡C-C(CH₃)(OH)-(CH₂)₄- | —(CH₂)₃—CH₃ | —(CH₂)₂—CH₃ | Hydrochloride | 126 |
| 17 | CH₃—(CH₂)₂— | —CH₃ | —(CH₂)₄-C(CH₃)(OH)-C≡C-CH₂-N(C₂H₅)₂ | Hydrochloride | 127 |
| 18 | (C₂H₅)₂N-CH₂-C≡C-C(CH₃)(OH)-(CH₂)₄- | —CH₃ | —(CH₂)₄-C(CH₃)(OH)-C≡C-CH₂-N(C₂H₅)₂ | Base | Oil |

TABLE 1-continued

Compounds of the formula I

| Ex. | R¹ | R² | R³ | isolated as | M.p.[°C.] |
|---|---|---|---|---|---|
| 19 | H₇C₃\N(CH₃)-CH₂-C≡C-C(CH₃)(OH)-(CH₂)₃- | —CH₃ | —H | Base | Oil |
| 20 | (C₂H₅)₂N-CH₂-C≡C-C(CH₃)(OH)-(CH₂)₄- | cyclopropyl | —(CH₂)₂—CH₃ | Hydrochloride | 146 |
| 21 | (C₂H₅)₂N-CH₂-C≡C-CH(OH)-(CH₂)₄- | —CH₃ | —(CH₂)₂—CH₃ | Hydrochloride | 65 |
| 22 | H₂N-CH₂-C≡C-C(CH₃)(OH)-(CH₂)₄- | —CH₃ | —(CH₂)₂—CH₃ | Hydrochloride | 80 |
| 23 | (C₂H₅)(H)N-CH₂-C≡C-C(CH₃)(OH)-(CH₂)₄- | —CH₃ | —(CH₂)₂—CH₃ | Base / Fumarate | Oil / 139 |

TABLE 1-continued
Compounds of the formula I
| Ex. | R¹ | R² | R³ | isolated as | M.p.[°C.] |
|---|---|---|---|---|---|
| 24 | 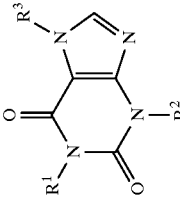 | —CH₃ | —(CH₂)₂—CH₃ | Base Hydrochloride | Oil 148 |
| 25 | 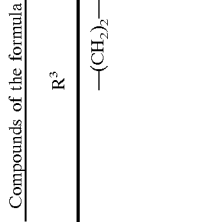 | —(CH₂)₂—CH₃ | —(CH₂)₂—CH₃ | Hydrochloride | 110 |
| 26 | 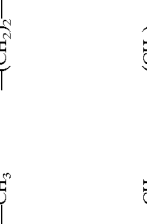 | —(CH₂)₂—CH₃ | —(CH₂)₂—CH₃ | Iodide | 51 (Decomp.) |
| 27 |  | —CH₃ | —(CH₂)₂—CH₃ | Iodide | 85 |
| 28 | 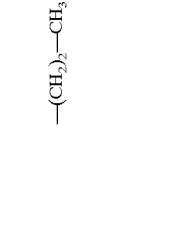 | —CH₃ | —(CH₂)₂—CH₃ | Hydrochloride | 105 |

TABLE 1-continued

Compounds of the formula I

| Ex. | R$^1$ | R$^2$ | R$^3$ | isolated as | M.p.[°C.] |
|---|---|---|---|---|---|
| 29 | pyrrolidin-1-yl-CH$_2$-C≡C-C(CH$_3$)(OH)-CH$_2$- | —(CH$_2$)$_2$—CH$_3$ | —(CH$_2$)$_2$—CH$_3$ | Hydrochloride | 140 |
| 30 | 1-methylpyrrolidinium-1-yl-CH$_2$-C≡C-C(CH$_3$)(OH)-CH$_2$- | —CH$_3$ | —(CH$_2$)$_2$—CH$_3$ | Iodide | 85 |
| 31 | piperazin-1-yl-CH$_2$-C≡C-C(CH$_3$)(OH)-CH$_2$- | —(CH$_2$)$_2$—CH$_3$ | —(CH$_2$)$_2$—CH$_3$ | Fumarate | 85 |
| 32 | (CH$_3$)$_2$N-CH$_2$-C≡C-C(CH$_3$)(OH)-(CH$_2$)$_2$- | —C$_2$H$_5$ | —(CH$_2$)$_2$—CH$_3$ | Hydrochloride | 102 |
| 33 | (CH$_3$)$_2$N-CH$_2$-C≡C-C(CH$_3$)(OH)-(CH$_2$)$_2$- | —(CH$_2$)$_2$—CH$_3$ | —(CH$_2$)$_2$—CH$_3$ | Hydrochloride | 85 |

TABLE 1-continued

Compounds of the formula I

| Ex. | R¹ | R² | R³ | isolated as | M.p.[°C.] |
|---|---|---|---|---|---|
| 34 | (CH₂)₂—C≡C—CH(OH)—CH₂—N(Et)₂ | —CH₃ | —(CH₂)₂—CH₃ | Base<br>Hydrochloride | 108<br>162 (Decomp.) |
| 35 | (CH₂)₂—C≡C—C(CH₃)(OH)—CH₂—N(CH₃)₂ | —(CH₂)₃—CH₃ | —(CH₂)₂—CH₃ | Base | Oil |
| 36 | (CH₂)₂—C≡C—C(CH₃)(OH)—CH₂—N(Et)₂ | —CH₃ | —(CH₂)₂—CH₃ | Base | 107 |
| 37 | (CH₂)₂—C≡C—C(CH₃)(OH)—CH₂—N(Et)₂ | —C₂H₅ | —(CH₂)₂—CH₃ | Hydrochloride | 110 |
| 38 | (CH₂)₂—C≡C—C(CH₃)(OH)—CH₂—N(Et)₂ | —(CH₂)₂—CH₃ | —(CH₂)₂—CH₃ | Base<br>Hydrochloride | 118<br>122 |

TABLE 1-continued

Compounds of the formula I

| Ex. | $R^1$ | $R^2$ | $R^3$ | isolated as | M.p.[°C.] |
|---|---|---|---|---|---|
| 39 | —CH$_2$—C≡C—CH(OH)—(CH$_2$)$_2$—N$^+$(C$_2$H$_5$)$_3$ | —CH$_3$ | —(CH$_2$)$_2$—CH$_3$ | Iodide | Oil |
| 40 | —CH$_2$—C≡C—C(CH$_3$)(OH)—(CH$_2$)$_2$—N$^+$(C$_2$H$_5$)$_3$ | —C$_2$H$_5$ | —(CH$_2$)$_2$—CH$_3$ | Iodide | 145 |
| 41 | —CH$_2$—C≡C—C(CH$_3$)(OH)—(CH$_2$)$_2$—N(CH$_3$)(C$_3$H$_7$) | —CH$_3$ | —(CH$_2$)$_2$—CH$_3$ | Hydrochloride | 208 |
| 42 | —CH$_2$—C≡C—C(CH$_3$)(OH)—(CH$_2$)$_2$—N(CH$_3$)(C$_3$H$_7$) | —C$_2$H$_5$ | —(CH$_2$)$_2$—CH$_3$ | Hydrochloride | 161 |
| 43 | —CH$_2$—C≡C—C(CH$_3$)(OH)—(CH$_2$)$_2$—N(CH$_3$)(C$_3$H$_7$) | cyclopropyl | —(CH$_2$)$_2$—CH$_3$ | Hydrochloride | 162 |

TABLE 1-continued

Compounds of the formula I

| Ex. | R¹ | R² | R³ | isolated as | M.p.[°C.] |
|---|---|---|---|---|---|
| 44 | H₉C₄—N(C₄H₉)—(CH₂)₂—C≡C—C(CH₃)(OH)— | cyclopropyl | —(CH₂)₂—CH₃ | Hydrochloride | 75 |
| 45 | H₉C₄—N⁺(CH₃)(C₄H₉)—(CH₂)₂—C≡C—C(CH₃)(OH)— | —CH₃ | —(CH₂)₂—CH₃ | Iodide | Oil |
| 46 | pyrrolidinyl—(CH₂)₂—C≡C—C(CH₃)(OH)— | —CH₃ | —(CH₂)₂—CH₃ | Fumarate | 123 |
| 47 | pyrrolidinyl—(CH₂)₂—C≡C—C(H)(OH)— | —C₂H₅ | —(CH₂)₂—CH₃ | Base | Oil |
| 48 | pyrrolidinyl—(CH₂)₂—C≡C—C(CH₃)(OH)— | —(CH₂)₂—CH₃ | —(CH₂)₂—CH₃ | Fumarate | 119 |

TABLE 1-continued
Compounds of the formula I
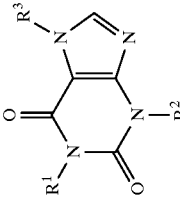
| Ex. | R¹ | R² | R³ | isolated as | M.p.[°C.] |
|---|---|---|---|---|---|
| 49 | 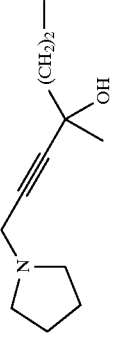 | —(CH$_2$)$_3$—CH$_3$ | —(CH$_2$)$_2$—CH$_3$ | Hydrochloride | 101 |
| 50 | 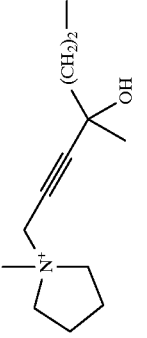 | —C$_2$H$_5$ | —(CH$_2$)$_2$—CH$_3$ | Iodide | 180 |
| 51 |  | —CH$_3$ | —(CH$_2$)$_2$—CH$_3$ | Hemifumarate | 166 |
| 52 |  | —CH$_3$ | —(CH$_2$)$_2$—CH$_3$ | Base | 108 |
| 53 |  | —CH$_3$ | —(CH$_2$)$_2$—CH$_3$ | Iodide | 169 |

TABLE 1-continued

Compounds of the formula I

| Ex. | R¹ | R² | R³ | isolated as | M.p.[°C.] |
|---|---|---|---|---|---|
| 54 | (4-methylpiperazinyl)-CH₂-C≡C-C(CH₃)(OH)-(CH₂)₂- | —CH₃ | —(CH₂)₂—CH₃ | Fumarate / Base | 80 / 118 |
| 55 | (4-methylpiperazinyl)-CH₂-C≡C-C(CH₃)(OH)-(CH₂)₂- | —C₂H₅ | —(CH₂)₂—CH₃ | Hydrochloride | 165 |
| 56 | (4-methylpiperazinyl)-CH₂-C≡C-C(CH₃)(OH)-(CH₂)₂- | —(CH₂)₃—CH₃ | —(CH₂)₂—CH₃ | Hydrochloride | 152 |
| 57 | (CH₃)₂N-CH₂-C≡C-C(CH₃)(OH)-(CH₂)₃- | —CH₃ | —(CH₂)₂—CH₃ | Fumarate | 125 |
| 58 | (CH₃)₂N-CH₂-C≡C-C(CH₃)(OH)-(CH₂)₃- | —C₂H₅ | —(CH₂)₂—CH₃ | Fumarate | 70 |

TABLE 1-continued

Compounds of the formula I

| Ex. | R¹ | R² | R³ | isolated as | M.p.[°C.] |
|---|---|---|---|---|---|
| 59 | CH₃-C(OH)(CH₂)₃-, C≡C-CH₂-N(CH₃)₂ | —(CH₂)₂—CH₃ | —(CH₂)₂—CH₃ | Hydrochloride | 153 |
| 60 | H-C(OH)(CH₂)₃-, C≡C-CH₂-N(C₂H₅)₂ | —CH₃ | —(CH₂)₂—CH₃ | Fumarate | 76 |
| 61 | H-C(OH)(CH₂)₃-, C≡C-CH₂-N(C₂H₅)₂ | —C₂H₅ | —(CH₂)₂—CH₃ | Hydrochloride | 128 |
| 62 | CH₃-C(OH)(CH₂)₃-, C≡C-CH₂-N(C₂H₅)₂ | —CH₃ | —(CH₂)₂—CH₃ | Fumarate | 140 |
| 63 | CH₃-C(OH)(CH₂)₃-, C≡C-CH₂-N(C₂H₅)₂ | —C₂H₅ | —(CH₂)₂—CH₃ | Base | 99 |

TABLE 1-continued

Compounds of the formula I

| Ex. | R¹ | R² | R³ | isolated as | M.p.[°C.] |
|---|---|---|---|---|---|
| 64 | –CH₂–C≡C–C(CH₃)(OH)–(CH₂)₃– with N⁺(Et)₂CH₃ | –CH₃ | –(CH₂)₂–CH₃ | Iodide | Oil |
| 65 | –CH₂–C≡C–C(CH₃)(OH)–(CH₂)₃– with N⁺(Et)₃ | –C₂H₅ | –(CH₂)₂–CH₃ | Iodide | 145 |
| 66 | –CH₂–C≡C–C(H)(OH)–(CH₂)₃– with N⁺(Et)₃ | –C₂H₅ | –(CH₂)₂–CH₃ | Iodide | Oil |
| 67 | –CH₂–C≡C–C(CH₃)(OH)–(CH₂)₃– with N⁺(Et)₃ | –(CH₂)₂–CH₃ | –(CH₂)₂–CH₃ | Hydrochloride | 137 |
| 68 | –CH₂–C≡C–C(CH₃)(OH)–(CH₂)₃– with N⁺(Et)₃ | –(CH₂)₂–CH₃ | –(CH₂)₂–CH₃ | Iodide | 145 |

TABLE 1-continued

Compounds of the formula I

| Ex. | R¹ | R² | R³ | isolated as | M.p.[°C.] |
|---|---|---|---|---|---|
| 69 | H₇C₃—N(C₃H₇)—(CH₂)₃—C≡C—C(CH₃)(OH)— | —CH₃ | —(CH₂)₂—CH₃ | Hydrochloride | 135 |
| 70 | H₇C₃—N(C₃H₇)—(CH₂)₃—C≡C—C(CH₃)(OH)— | —(CH₂)₂—CH₃ | —(CH₂)₂—CH₃ | Hydrochloride | 119 |
| 71 | H₇C₃—N⁺(C₃H₇)(C₂H₅)—(CH₂)₃—C≡C—C(CH₃)(OH)— | —(CH₂)₂—CH₃ | —(CH₂)₂—CH₃ | Iodide | Oil |
| 72 | H₉C₄—N(C₄H₉)—(CH₂)₃—C≡C—C(CH₃)(OH)— | —CH₃ | —H | Base | Oil |
| 73 | H₉C₄—N(C₄H₉)—(CH₂)₃—C≡C—C(CH₃)(OH)— | —CH₃ | —(CH₂)₂—CH₃ | Base<br>Hydrochloride | 75<br>169 |

TABLE 1-continued

Compounds of the formula I

| Ex. | R¹ | R² | R³ | isolated as | M.p.[°C.] |
|---|---|---|---|---|---|
| 74 | H₉C₄—N⁺(CH₃)(C₄H₉)—(CH₂)₃—C≡C—C(CH₃)(OH)— | —CH₃ | —H | Iodide | 139 |
| 75 | H₉C₄—N⁺(CH₃)(C₄H₉)—(CH₂)₃—C≡C—C(CH₃)(OH)— | —CH₃ | —(CH₂)₂—CH₃ | Iodide | 157 |
| 76 | PhCH₂—N(CH₃)—CH₂—C≡C—C(CH₃)(OH)—(CH₂)₃— | —CH₃ | —(CH₂)₂—CH₃ | Base | Oil |
| 77 | Pyrrolidin-1-yl—CH₂—C≡C—CH(OH)—(CH₂)₃— | —CH₃ | —(CH₂)₂—CH₃ | Hydrochloride | 71 |
| 78 | Pyrrolidin-1-yl—CH₂—C≡C—CH(OH)—(CH₂)₃— | —C₂H₅ | —(CH₂)₂—CH₃ | Hydrochloride | 88 |

TABLE 1-continued
Compounds of the formula I
| Ex. | R¹ | R² | R³ | isolated as | M.p.[°C.] |
|---|---|---|---|---|---|
| 79 | 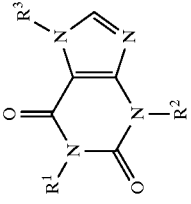 | —CH₃ | —(CH₂)₂—CH₃ | Hemifumarate | 186 |
| 80 |  | —C₂H₅ | —(CH₂)₂—CH₃ | Hydrochloride | 78 |
| 81 |  | —(CH₂)₂—CH₃ | —(CH₂)₂—CH₃ | Fumarate | 85 |
| 82 |  | —CH₃ | —(CH₂)₂—CH₃ | Iodide | Oil |
| 83 | 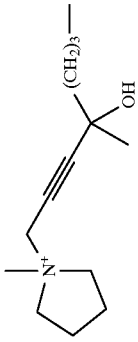 | —C₂H₅ | —(CH₂)₂—CH₃ | Iodide | 100 |

TABLE 1-continued
Compounds of the formula I
| Ex. | R[1] | R[2] | R[3] | isolated as | M.p.[°C.] |
|---|---|---|---|---|---|
| 84 |  | —C$_2$H$_5$ | —(CH$_2$)$_2$—CH$_3$ | Iodide | Oil |
| 85 |  | —(CH$_2$)$_2$—CH$_3$ | —(CH$_2$)$_2$—CH$_3$ | Iodide | 118 |
| 86 |  | —CH$_3$ | —(CH$_2$)$_2$—CH$_3$ | Hemifumarate | 198 |
| 87 |  | —CH$_3$ | —(CH$_2$)$_2$—CH$_3$ | Hemifumarate | 178 |
| 88 |  | —CH$_3$ | —(CH$_2$)$_2$—CH$_3$ | Iodide | 121 |

TABLE 1-continued

Compounds of the formula I

| Ex. | R¹ | R² | R³ | isolated as | M.p.[°C.] |
|---|---|---|---|---|---|
| 89 | 4-methylpiperazinyl-(CH₂)₃-C(CH₃)(OH)- | —C₂H₅ | —(CH₂)₂—CH₃ | Hydrochloride | 103 |
| 90 | 4-methylpiperazinyl-(CH₂)₃-C(CH₃)(OH)- | —(CH₂)₂—CH₃ | —(CH₂)₂—CH₃ | Fumarate | 132 |
| 91 | 1,4-dimethylpiperazinium-(CH₂)₃-C(CH₃)(OH)- | —CH₃ | —(CH₂)₂—CH₃ | Iodide | hygr. |
| 92 | (CH₃)₂N-(CH₂)₄-C(CH₃)(OH)- | —CH₃ | —(CH₂)₂—CH₃ | Hemifumarate | 137 |
| 93 | (CH₃)₂N-(CH₂)₄-C(CH₃)(OH)- | —(CH₂)₂—CH₃ | —(CH₂)₂—CH₃ | Fumarate | 89 |

TABLE 1-continued

Compounds of the formula I

| Ex. | R¹ | R² | R³ | isolated as | M.p.[°C.] |
|---|---|---|---|---|---|
| 94 | (CH₃)₃N⁺—CH₂—C≡C—C(CH₃)(OH)—(CH₂)₄— | —(CH₂)₂—CH₃ | —(CH₂)₂—CH₃ | Iodide | 127 |
| 95 | (C₂H₅)₂N—CH₂—C≡C—C(CH₃)(OH)—(CH₂)₄— | —C₂H₅ | —(CH₂)₂—CH₃ | Hydrochloride | 75 |
| 96 | (C₂H₅)₂N—CH₂—C≡C—CH(OH)—(CH₂)₄— | —C₂H₅ | —(CH₂)₂—CH₃ | Hydrochloride | 110 |
| 97 | (C₂H₅)₂N—CH₂—C≡C—C(CH₃)(OH)—(CH₂)₄— | —(CH₂)₂—CH₃ | —(CH₂)₂—CH₃ | Hydrochloride | 128 |
| 98 | (C₂H₅)₂N—CH₂—C≡C—C(CH₃)(OH)—(CH₂)₄— | —(CH₂)₃—CH₃ | —(CH₂)₂—CH₃ | Hydrochloride | 97 |

TABLE 1-continued

Compounds of the formula I

| Ex. | R¹ | R² | R³ | isolated as | M.p.[°C.] |
|---|---|---|---|---|---|
| 99 | (CH₂)₄-C(CH₃)(OH)-C≡C-CH₂-N⁺(C₂H₅)₃ | —CH₃ | —(CH₂)₂—CH₃ | Iodide | 118 |
| 100 | (CH₂)₄-C(CH₃)(OH)-C≡C-CH₂-N⁺(C₂H₅)₃ | —C₂H₅ | —(CH₂)₂—CH₃ | Iodide | 175 |
| 101 | (CH₂)₄-C(CH₃)(OH)-C≡C-CH₂-N⁺(C₂H₅)₃ | —(CH₂)₂—CH₃ | —(CH₂)₂—CH₃ | Iodide | 148 |
| 102 | (CH₂)₄-C(CH₃)(OH)-C≡C-CH₂-N⁺(C₂H₅)₃ | —(CH₂)₃—CH₃ | —(CH₂)₂—CH₃ | Iodide | 130 |
| 103 | (CH₂)₄-C(CH₃)(OH)-C≡C-CH₂-N⁺(C₂H₅)₃ | —CH₃ | —(CH₂)₂—CH₃ | Iodide | 193 |

TABLE 1-continued

Compounds of the formula I (structure: xanthine core with R¹ on N1, R² on N3, R³ on N7)

| Ex. | R¹ | R² | R³ | isolated as | M.p.[°C.] |
|---|---|---|---|---|---|
| 104 | H₃C–N(C₃H₇)–CH₂–C≡C–C(CH₃)(OH)–(CH₂)₄– | —CH₃ | —H | Base | Oil |
| 105 | H₃C–N(C₃H₇)–CH₂–C≡C–C(CH₃)(OH)–(CH₂)₄– | —CH₃ | —(CH₂)₂—CH₃ | Hydrochloride | 161 |
| 106 | H₃C–N(C₃H₇)–CH₂–C≡C–C(CH₃)(OH)–(CH₂)₄– | —C₂H₅ | —(CH₂)₂—CH₃ | Hydrochloride | 173 |
| 107 | H₃C–N(C₃H₇)–CH₂–C≡C–C(CH₃)(OH)–(CH₂)₄– | —(CH₂)₂—CH₃ | —(CH₂)₂—CH₃ | Hydrochloride | 138 |
| 108 | H₃C–N(C₃H₇)–CH₂–C≡C–C(CH₃)(OH)–(CH₂)₄– | cyclopropyl | —(CH₂)₂—CH₃ | Hydrochloride | 213 |

TABLE 1-continued

Compounds of the formula I

| Ex. | R¹ | R² | R³ | isolated as | M.p.[°C.] |
|---|---|---|---|---|---|
| 119 | pyrrolidinium-(CH₂)₄-C(OH)(CH₃)-C≡C-CH₂- | —C₂H₅ | —(CH₂)₂—CH₃ | Iodide | 82 |
| 120 | pyrrolidinium-(CH₂)₄-C(OH)(H)-C≡C-CH₂- | —C₂H₅ | —(CH₂)₂—CH₃ | Iodide | 79 |
| 121 | pyrrolidinium-(CH₂)₄-C(OH)(CH₃)-C≡C-CH₂- | —(CH₂)₂—CH₃ | —(CH₂)₂—CH₃ | Iodide | 104 |
| 122 | piperidinyl-(CH₂)₄-C(OH)(CH₃)-C≡C-CH₂- | —CH₃ | —(CH₂)₂—CH₃ | Hydrochloride | 129 |
| 123 | piperidinyl-(CH₂)₄-C(OH)(CH₃)-C≡C-CH₂- | cyclopropyl | —(CH₂)₂—CH₃ | Base | Oil |

TABLE 1-continued

Compounds of the formula I

| Ex. | R$^1$ | R$^2$ | R$^3$ | isolated as | M.p.[°C.] |
|---|---|---|---|---|---|
| 124 | N-piperidinium-CH$_2$-C≡C-C(CH$_3$)(OH)-(CH$_2$)$_4$- | —(CH$_2$)$_3$—CH$_3$ | —(CH$_2$)$_2$—CH$_3$ | Iodide | 117 |
| 125 | N-morpholino-CH$_2$-C≡C-C(CH$_3$)(OH)-(CH$_2$)$_4$- | —CH$_3$ | —(CH$_2$)$_2$—CH$_3$ | Hydrochloride | 131 |
| 126 | 4-methylpiperazin-1-yl-CH$_2$-C≡C-C(CH$_3$)(OH)-(CH$_2$)$_4$- | —CH$_3$ | —(CH$_2$)$_2$—CH$_3$ | Fumarate | 97 |
| 127 | 4-methylpiperazin-1-yl-CH$_2$-C≡C-C(CH$_3$)(OH)-(CH$_2$)$_4$- | —C$_2$H$_5$ | —(CH$_2$)$_2$—CH$_3$ | Fumarate | 80 |
| 128 | 1,4-dimethylpiperazinium-CH$_2$-C≡C-C(CH$_3$)(OH)-(CH$_2$)$_4$- | —CH$_3$ | —(CH$_2$)$_2$—CH$_3$ | Iodide | hygr. |

TABLE 1-continued

Compounds of the formula I

| Ex. | R¹ | R² | R³ | isolated as | M.p.[°C.] |
|---|---|---|---|---|---|
| 129 | ![structure: piperazine-N-acetyl connected via -CH₂-C≡C-C(CH₃)(OH)-(CH₂)₄-] | —CH₃ | —(CH₂)₂—CH₃ | Base | Oil |
| 130 | (CH₃)₂N—CH₂-C≡C-C(CH₃)(OH)-(CH₂)₅— | —CH₃ | —(CH₂)₂—CH₃ | Base | Oil |

M.p. stands for melting point
hygr. stands for hygroscopic

TABLE 2

Compounds of the formula IX:

| Example | R⁹ | R² | R¹⁰ | M.p.[°C.] |
|---|---|---|---|---|
| 131 | HC≡C-C(CH₃)(OH)-(CH₂)₂- | -CH₃ | -(CH₂)₂-CH₃ | 149 |
| 132 | HC≡C-C(CH₃)(OH)-(CH₂)₃- | -CH₃ | -(CH₂)₂-CH₃ | 108 |
| 133 | HC≡C-C(CH₃)(OH)-(CH₂)₃- | -C₂H₅ | -(CH₂)₂-CH₃ | 78 |
| 134 | HC≡C-C(CH₃)(OH)-(CH₂)₄- | -CH₃ | -H | 172 |
| 135 | HC≡C-C(CH₃)(OH)-(CH₂)₄- | -CH₃ | -CH₃ | 121 |
| 136 | HC≡C-C(CH₃)(OH)-(CH₂)₄-<br>Racemate | -CH₃ | -(CH₂)₂-CH₃ | 98 |
| 136a | HC≡C-C(CH₃)(OH)-(CH₂)₄-<br>(+)-Enantiomer | -CH₃ | -(CH₂)₂-CH₃<br>$[\alpha]_D^{20} = -6.05$<br>(CHCl₃; c = 6.0) | 75 |
| 136b | HC≡C-C(CH₃)(OH)-(CH₂)₄-<br>(+)-Enantiomer | -CH₃ | -(CH₂)₂-CH₃<br>$[\alpha]_D^{20} = +5.97$<br>(CHCl₃; c = 11.6) | 75 |
| 137 | HC≡C-C(CH₃)(OH)-(CH₂)₄- | -C₂H₅ | -(CH₂)₂-CH₃ | 96 |

TABLE 2-continued

Compounds of the formula IX:

| Example | R⁹ | R² | R¹⁰ | | M.p.[°C.] |
|---|---|---|---|---|---|
| 138 | —H | —CH₃ | —(CH₂)₄—C(OH)(—)—C≡C—H | | 173 |
| 139 | H₃C—(CH₂)₂— | —CH₃ | —(CH₂)₄—C(OH)(—)—C≡C—H | | 97 |
| 140 | H—C≡C—C(OH)(—)—(CH₂)₅— | —CH₃ | —(CH₂)₂—CH₃ | | 79 |

It was possible to demonstrate the pronounced neuronal protective effect of the compounds of the formula I in animal experimental suitability models which are clinically relevant, including the xanthine derivative propentofylline (3-methyl-1-(5-oxohexyl)-7-propylxanthine) as comparison product in the investigations.

The test results demonstrated that the compounds according to the invention are distinctly superior to the comparison product and, accordingly, have a greater therapeutic potential for curative and prophylactic treatment of cerebrovascular disorders.

1. Neuroprotective effect in the model of transient global ischemia in gerbils To carry out the experiment, which took place in accordance with the provisions of the German Animal Protection Act, 30 male Mongolian gerbils weighing between 60 and 70 g were distributed at random between two groups each of 15 animals. The animals in the first group received the particular test substance by intraperitoneal injection 30 minutes after the ischemic period, while the animals in the second group, which served as untreated control group, merely received the same volume of the relevant vehicle.

To produce the temporary forebrain ischemia, the animals were anesthetized with halothane and fixed supine on a heated operating stage, and both common carotid arteries were cautiously exposed and closed for 3 minutes using microaneurysm clips (J. Cereb. Blood Flow Metab. 1987, 7/1: 74–81). 7 Days after the 3-minute ischemic period, the animals were anesthetized with halothane and decapitated, the brains were rapidly and carefully removed, first immersion-fixed in Carnoy's solution (ethanol/chloroform/acetic acid 6:3:1) and then embedded in paraffin, and subsequently coronal sections 4 to 6 μm thick through the hippocampus approximately at the level of the bregma were produced and stained with hematoxylin and eosin. Then, in a blind test, the extent of the eosinophilic necroses of the pyramidal cells in the CA1region of the hippocampus was determined under the light microscope using a semiquantitative histopathological score (0=none; 1=slight; 2=moderate; 3=severe and 4=complete necroses). The quantity used for assessing the neuroprotective effect was the percentage change in the average histopathological score in the product group compared with that for the untreated control group. The experimental results are compiled in Table 3.

TABLE 3

Inhibition of ischemic nerve cell damage in the Mongolian gerbil

| Compound of example | Dose in mg/kg | Inhibition of neuronal CA1 hippocampus damage in % |
|---|---|---|
| 1 | 10 | 31 |
| 1 | 5 | 19 |
| 2 | 10 | 49 |
| 3 | 10 | 30 |
| 4 | 10 | 45 |
| 4 | 5 | 39 |
| 6 | 10 | 30 |
| 13 | 10 | 36 |
| 14 | 10 | 48 |
| 18 | 10 | 38 |
| 21 | 10 | 38 |
| 25 | 10 | 54 |
| 32 | 10 | 48 |
| 41 | 10 | 42 |
| 44 | 10 | 39 |
| 52 | 10 | 31 |
| 62 | 10 | 22 |
| 63 | 10 | 50 |
| 77 | 10 | 39 |

TABLE 3-continued

Inhibition of ischemic nerve cell damage in the Mongolian gerbil

| Compound of example | Dose in mg/kg | Inhibition of neuronal CA1 hippocampus damage in % |
|---|---|---|
| 87 | 10 | 39 |
| 94 | 10 | 25 |
| 97 | 10 | 34 |
| 107 | 10 | 30 |
| 110 | 10 | 32 |
| 111 | 10 | 34 |
| 112 | 10 | 21 |
| 124 | 10 | 31 |
| 126 | 10 | 36 |
| 129 | 10 | 45 |
| 137 | 10 | 38 |
| Propentofylline (comparison) | 10 | 19 |

It was also possible to demonstrate convincingly the surprisingly good neuroprotective activity of the compounds of the formula I according to the invention in the experimental designs which are described hereinafter but involve a more elaborate methodological technique.

2. Inhibitory effect on neurological symptoms in the model of permanent focal cerebral ischemia in rats The experimental animals were adult male Sprague-Dawley rats weighing 300 to 400 g with a focal cerebral infarct produced experimentally by permanent occlusion of the middle cerebral artery (MCA) (J. Cereb. Blood Flow Metab. 1981, 1: 53–60).

The surgical preparation took about 20 to 30 minutes and was performed under anesthesia with nitrous oxide containing 1 to 1.2% halothane, which was admixed with the air breathed through a gas mask with spontaneous breathing. After catheterization of the right femoral artery and vein for measuring the blood pressure, taking blood samples and later administering the test substance, the occlusion of the left MCA was brought about under powerful magnification by a surgical microscope, via the subtemporal access without removing the zygomatic arch and temporal muscles, by electrocoagulation and subsequent vessel severance, the progress of the operation being monitored by continuous recording of the average arterial blood pressure by means of an electromechanical pressure transducer (Model 7E Polygraph; Grass, USA). After the operation, the animals were allowed to recover from the anesthesia and their body temperature was maintained in the normal range around 37° C. using a homeothermic heating drape (Homeothermic Blanket System; Harvard Apparatus, UK).

Fifteen minutes after the vessel occlusion, the animals in the product group (n=8) received the test substance administered in the form of an intraperitoneal bolus injection of 10 mg/kg as initial dose and continued treatment by a 24-hour continuous infusion of 0.1 mg/kg/min through the venous catheter using a special, freely rotatable turnbuckle system (Harvard Apparatus, UK), while the animals in the untreated control group (n=7) received only the vehicle (physiological saline) by the same route. 15 minutes before and immediately after the vessel occlusion, and shortly after the start of the continuous infusion of the test product or of the vehicle, the arterial blood gases and the pH (178 pH/blood gas analyzer; Corning, USA) and the hematocrit and blood glucose level were checked to detect physiological irregularities; it was then possible to remove the arterial catheter. In addition, the temperature of the temporal muscles on both sides (Therm 2250-1; Ahlborn Meβ-und Regeltechnik, FRG), and the rectal body temperature, were measured from the start of the operation up to 10 minutes after the start of the continuous infusion and for a few minutes before the end of the experiment. 24 hours after the vessel occlusion, the continuous infusion was stopped, and the extent of the neurological deficit caused by the ischemia was determined using the four-point symptom scale of Bederson et al. (Stroke 1986, 17: 422–476) with the following assessment criteria:

0=no signs of neurological deficits;
1=front extremities held flexed;
2=diminished resistance to a push from the side without moving in a circle;
3=same symptoms as for 2, but with moving in a circle.

For biostatistical analysis of the experimental data, the frequency distribution of the neurological scores in the product and control groups was compared using Student's t test (significance level $p<0.5$). In this, for example, the compound of Example 1 caused a significant reduction ($p<0.01$) in the neurological deficit ($1.1\pm0.4$; average$\pm$SD) compared with that in the untreated control animals ($2.3\pm0.5$; average$\pm$SD), corresponding to an improvement in the neurological status by 52% without any adverse effect on the investigated physiological parameters being evident.

3. Neuroprotective effect on the model of permanent focal cerebral ischemia in rats The experimental design very substantially corresponded to the method described in Experiment 2. The product and control groups comprised n=6 animals in each case. However, dispensing with the rather complicated continuous intravenous infusion on the conscious animal, the test substances were administered entirely intraperitoneally, specifically by three administrations of 10 mg/kg in each case at intervals of 15 minutes, 3 and 6 hours after the surgical MCA occlusion. After the experiment had lasted 24 hours, the animals were decapitated under anesthesia, the brains were rapidly and carefully removed and frozen at $-10°$ C. for 10 minutes, and subsequently the forebrains were sliced into 8 coronal sections in defined planes, the sections being stained by the cresyl staining technique. Then, in a blind experiment, the infarcted areas, which could not be stained, of the coronal sections were transferred onto a graph and measured by planimetry, and the infarct volume in the left cerebral hemisphere which was affected by the ischemia was determined by integration of all the areas (Neurosci. Lett. 1992, 147: 41–44). The significance (level<0.05) of the differences between the untreated control group and the product groups was the assessed using Student's t test.

On testing the compounds according to the invention in a direct comparison with propentofylline, for example, the product from Preparation example 1 led, after intraperitoneal administration of 3×10 mg/kg (equivalent to 3×22 $\mu$mol/kg), to a statistically significant ($p<0.05$) 56% reduction in the infarct volume ($99\pm17\,\mu$l; average$\pm$SD) compared with that in the untreated control group ($222\pm43\,\mu$l; average$\pm$SD), while the comparison product propentofylline, likewise at a dose of 3×10 mg/kg (equivalent to 3×33 $\mu$mol/kg), brought about a 43% reduction ($127\pm28\,\mu$l; average$\pm$SD).

4. Neuroprotective effect in the model of permanent focal cerebral ischemia in mice In this experimental design, the effect of the compounds of the formula I, compared with that of propentofylline as reference substance, on the necrotic damage to the surface of the cerebral cortex after permanent occlusion of the right MCA was investigated as representing a reliable measure of the infarct volume (J. Pharmacol. Methods 1992, 27: 27–32).

The experimental animals were male Swiss CD1 mice with a body weight between 33 and 40 g, whose right MCA was occluded by a surgical intervention in analogy to Experiment 2 under chloral hydrate anesthesia (400 mg/kg i.p.). Four mice were subjected to a sham operation in which the MCA was exposed in the same way but not occluded; these animals formed the control group intended to quantify any effect of the surgical operation on the damage to nerve cells. Since both anesthesia and ischemia usually induce hypothermia, which may lead to a reduction in the infarct size (Brain Res. 1992, 587: 66–72), the temporal muscle temperature was kept in the normal range around 37° C. during the surgical manipulation using a halogen heating lamp, as was the body temperature throughout the experiment by appropriate adjustment of the ambient temperature. 5 minutes and 3 and 6 hours after the MCA occlusion, the particular test substance, dissolved in distilled water, was administered to the animals in the product group (n=12) by intraperitoneal (i.p.) injection of 10 mg/kg in each case, while the animals in the placebo group (n=12) received only the vehicle, and the mice in the control group (n=4) received neither product nor vehicle. 24 hours after the vessel occlusion, the animals were decapitated under isoflurane anesthesia, and the brains were removed and stained within 30 to 40 minutes in 2% strength aqueous 2,3,5-triphenyltetrazolium chloride (TTC) solution at 37° C. The cerebral cortex was then isolated from the right hemisphere, and the infarct area, which was not stainable by TTC, was measured by image analysis (BIOCOM). Statistical analysis of the experimental results took place with the Kruskal-Wallis and Mann-Whitney non-parametric tests. It emerged from this that virtually no necroses occurred in the cortex of the mice in the control group with the sham operation, whereas the vehicle-treated animals in the placebo group showed significant neuronal damage resulting from the focal ischemia, with an infarct area of $31.3\pm1.7$ mm$^2$ (average$\pm$SD; p=0.0002).

It was possible to reduce this damage significantly by 38% to $19.3\pm1.5$ mm$^2$ (average$\pm$SD; p=0.0001) using the compound of Example 1, whereas a damage limitation of only 20%, to $25.2\pm2.1$ mm$^2$ (average$\pm$SD; p=0.0153), was achieved with propentofylline as comparison product. Since the difference between the two product groups was also statistically significant, with p<0.05, the compound according to the invention proved to have significantly greater neuroprotective activity than the comparison product.

We claim:

1. A compound of the formula I,

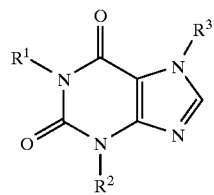

in stereoismerically pure form or as a mixture of stereoisomers, where

1) $R^1$ and $R^3$ are an alkynol residue of the formula Ia or Ib,

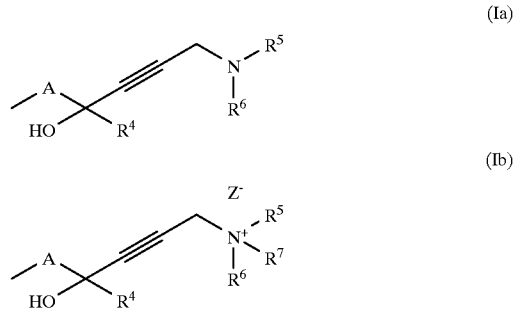

$R^2$ is
  a) straight-chain or branched ($C_1$–$C_5$)-alkyl,
  b) ($C_3$–$C_6$)-cycloalkyl or
  c) ($C_4$–$C_8$)-cycloalkylalkyl, $R^4$ is a hydrogen atom or ($C_1$–$C_3$)-alkyl, $R^5$, $R^6$ and $R^7$ are, independently of one another,
  a) a hydrogen atom,
  b) ($C_1$–$C_6$)-alkyl,
  c) ($C_3$–$C_6$)-cycloalkyl,
  d) ($C_4$–$C_8$)-cycloalkylalkyl,
  e) Ar-($C_1$–$C_2$)-alkyl or
  f) tri-($C_1$–$C_4$)-alkylsilyl, or $R^5$ and $R^6$, together with the nitrogen atom to which they are bonded, form a 4- to 7-membered saturated ring having the structure of pyrrolidine, piperidine, 4-($C_1$–$C_4$)-alkylpiperazine, azetidine, 2,5-dimethylpyrrolidine, 2,6-dimethylpiperidine, perhydroazepine, piperazine, 2,2,6,6-tetramethylpiperidine, thiomorpholine or its sulfoxide or sulfone, or morpholine;

A is unbranched or branched ($C_1$–$C_6$)-alkylene, and

Z is the anion of a physiologically tolerated inorganic or organic acid, or

2) $R^1$ or $R^3$ is an alkynol residue of the formula Ia or Ib, and the other radical $R^3$ or $R^1$ is
  a) a hydrogen atom or
  b) $R^8$, in which $R^8$ is straight-chain or branched ($C_1$–$C_6$)-alkyl, ($C_3$–$C_6$)-cycloalkyl or ($C_4$–$C_8$)-cycloalkylalkyl, and $R^2$, $R^4$, $R^5$, $R^6$, $R^7$, A and Z are as defined under 1).

2. A compound of claim 1, wherein only one of the two radicals $R^1$ or $R^3$ is an alkynol residue of the formula Ia or Ib, and the other radical is a hydrogen atom or $R^8$.

3. A compound of claim 2, wherein $R^1$ is an alkynol residue of the formula Ia or Ib and $R^3$ is a hydrogen atom or $R^8$.

4. A compound of claim 3, wherein $R^1$ is an alkynol residue of the formula Ia or Ib, $R^2$ is straight-chain ($C_1$–$C_4$)-alkyl, cyclopropyl or cyclopropylmethyl, $R^3$ is
  a) a hydrogen atom or b) $R^8$, in which $R^8$ is straight-chain or branched ($C_1$–$C_6$)-alkyl, cyclopropyl or cyclopropylmethyl, $R^4$ is a hydrogen atom, methyl or ethyl, $R^5$, $R^6$ and $R^7$ are, independently of one another, a hydrogen atom, ($C_1$–$C_4$)-alkyl, cyclopropyl, cyclopropylmethyl or benzyl, or $R^5$ and $R^6$ form, together with the nitrogen atom to which they are bonded, a 5- to 6-membered saturated ring from the group of morpholine, 4-($C_1$–$C_3$)-alkylcarbonylpiperazine, 4-($C_1$–$C_2$)-alkylpiperazine, piperazine, piperidine, pyrrolidine and thiomorpholine, A is unbranched ($C_1$–$C_5$)-alkylene, and $Z^-$ is the anion of a physiologically tolerated inorganic or organic acid.

5. A compound of claim 4, wherein $R^1$ is an alkynol residue of the formula Ia or Ib, $R^2$ is ($C_1$–$C_4$)-alkyl, $R^3$ is straight-chain ($C_2$–$C_4$)-alkyl or cyclopropyl, $R^4$ is a hydrogen atom or methyl, $R^5$, $R^6$ and $R^7$ are, independently of one another, a hydrogen atom, ($C_1$–$C_4$)-alkyl or benzyl, or $R^5$ and $R^6$ form, together with the nitrogen atom to which they are bonded, the morpholine, pyrrolidine, piperidine, 4-methylpiperazine or 4-acetylpiperazine ring, A is unbranched ($C_2$–$C_4$)-alkylene, and $Z^-$ is the anion of a physiologically tolerated inorganic or organic acid.

6. A compound of claim 5 which is 1-(8-diethylamino-5-hydroxy-5-methyl-6-octynyl)-3-methyl-7-propylxanthine and its physiologically tolerated acid addition salts.

7. A compound of claim 5 which is 1-(5-hydroxy-5-methyl-8-pyrrolidino-6-octynyl)-3-methyl-7-propylxanthine and its physiologically tolerated acid addition salts.

8. A compound of claim 5 which is 3-butyl-1-(5-hydroxy-5-methyl-8-piperidino-6-octynyl)-7-propylxanthine and its physiologically tolerated acid addition salts.

9. A compound of claim 5 which is 1-(5-diethylamino-2-hydroxy-2-methyl-3-pentynyl)-3-propyl-7-propylxanthine and its physiologically tolerated acid addition salts.

10. A compound of claim 5 which is 1-(6-dimethylamino-3-hydroxy-3-methyl-4-hexynyl)-3-ethyl-7-propylxanthine and its physiologically tolerated acid addition salts.

11. A compound of claim 5 which is 1-(7-diethylamino-4-hydroxy-4-methyl-5-heptynyl)-3-ethyl-7-propylxanthine and its physiologically tolerated acid addition salts.

12. A compound of claim 5 which is 1-[8-(4-acetylpiperazino)-5-hydroxy-5-methyl-6-octynyl]-3-methyl-7-propylxanthine and its physiologically tolerated acid addition salts.

13. A compound of claim 5 which is N,N-diethyl-N-[4-hydroxy-4-methyl-8-(3-methyl-7-propyl-1-xanthinyl)-2-octynyl]-N-methylammonium iodide.

14. A compound of the formula IX in stereoisomerically pure form or as a mixture of stereoisomers

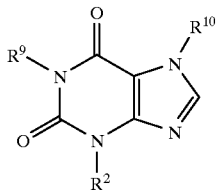

(IX)

wherein $R^9$ and $R^{10}$ are identical or different radicals of the formula IXa,

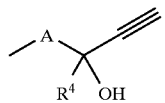

(IXa)

such that when $R^9$ and $R^{10}$ are different, one of $R^9$ and $R^{10}$ is hydrogen or $R^8$, wherein, $R^2$ is
   a) straight-chain or branched ($C_1$–$C_5$)-alkyl,
   b) ($C_3$–$C_6$)-cycloalkyl, or
   c) ($C_4$–$C_8$)-cycloalkylalkyl;

A is an unbranched or branched ($C_2$–$C_6$)-alkylene;

$R^4$ is a hydrogen atom or ($C_1$–$C_3$)-alkyl; and $R^8$ is straight-chain or branched ($C_1$–$C_6$)-alkyl, ($C_3$–$C_6$)-cycloalkyl, or ($C_4$–$C_8$)-cycloalkylalkyl.

15. A pharmaceutical composition comprising a compound as claimed in claim 1 and a pharmaceutically acceptable carrier therefor.

\* \* \* \* \*